US010526655B2

(12) United States Patent
Whitney et al.

(10) Patent No.: US 10,526,655 B2
(45) Date of Patent: Jan. 7, 2020

(54) METHODS FOR EVALUATING COPD STATUS

(71) Applicant: VERACYTE, INC., South San Francisco, CA (US)

(72) Inventors: Duncan H. Whitney, Sudbury, MA (US); Jun Luo, Belmont, MA (US)

(73) Assignee: Veracyte, Inc., South San Francisco, CA (US)

( * ) Notice: Subject to any disclaimer, the term of this patent is extended or adjusted under 35 U.S.C. 154(b) by 334 days.

(21) Appl. No.: 14/775,379

(22) PCT Filed: Mar. 13, 2014

(86) PCT No.: PCT/US2014/025715
§ 371 (c)(1),
(2) Date: Sep. 11, 2015

(87) PCT Pub. No.: WO2014/186036
PCT Pub. Date: Nov. 20, 2014

(65) Prior Publication Data
US 2016/0024583 A1   Jan. 28, 2016

Related U.S. Application Data

(60) Provisional application No. 61/783,983, filed on Mar. 14, 2013.

(51) Int. Cl.
*C12Q 1/6883* (2018.01)
*G16B 25/00* (2019.01)
*G16B 40/00* (2019.01)

(52) U.S. Cl.
CPC .......... *C12Q 1/6883* (2013.01); *G16B 25/00* (2019.02); *G16B 40/00* (2019.02); *C12Q 2600/158* (2013.01)

(58) Field of Classification Search
CPC ............ C12Q 1/6883; C12Q 2600/158; G01N 2800/122; G06F 19/20; G06F 19/24
See application file for complete search history.

(56) References Cited

U.S. PATENT DOCUMENTS 3,640,268 A   2/1972  Davis
4,641,662 A   2/1987  Jaicks
(Continued)

FOREIGN PATENT DOCUMENTS

CN   1688582 A       10/2005
DE   10219117 C1     10/2003
(Continued)

OTHER PUBLICATIONS

Li, X et al. American Journal of Respiratory and Critical Care Medicine 183(1 Supp.): abstract A6176 (May 1, 2011) (3 pages).*
(Continued)

*Primary Examiner* — Diana B Johannsen
(74) *Attorney, Agent, or Firm* — Wilson Sonsini Goodrich & Rosati

(57) ABSTRACT

The invention in some aspects provides methods of determining the likelihood that a subject has COPD based on the expression of informative-genes. In other aspects, the invention provides methods for determining an appropriate diagnostic intervention plan for a subject based on the expression of informative-genes. Related compositions and kits are provided in other aspects of the invention.

12 Claims, 1 Drawing Sheet

(56) References Cited

U.S. PATENT DOCUMENTS

| | | | |
|---|---|---|---|
| 4,800,896 A | 1/1989 | Jalowayski |
| 5,422,273 A | 6/1995 | Garrison et al. |
| 5,440,942 A | 8/1995 | Hubbard |
| 5,477,863 A | 12/1995 | Grant |
| 5,726,060 A | 3/1998 | Bridges |
| 5,795,782 A | 8/1998 | Church et al. |
| 5,876,978 A | 3/1999 | Willey et al. |
| 5,989,815 A | 11/1999 | Skolnick et al. |
| 6,013,431 A | 1/2000 | Soederlund et al. |
| 6,015,714 A | 1/2000 | Baldarelli et al. |
| 6,022,692 A | 2/2000 | Coulie et al. |
| 6,085,907 A | 7/2000 | Hochmeister et al. |
| 6,225,051 B1 | 5/2001 | Sugiyama et al. |
| 6,268,142 B1 | 7/2001 | Duff et al. |
| 6,627,067 B1 | 9/2003 | Branton et al. |
| 6,723,506 B2 | 4/2004 | Fletcher et al. |
| 6,746,846 B1 | 6/2004 | Wang et al. |
| 7,238,485 B2 | 7/2007 | Akeson et al. |
| 7,258,838 B2 | 8/2007 | Li et al. |
| 7,378,233 B2 | 5/2008 | Sidransky et al. |
| 7,407,755 B2 | 8/2008 | Lubinski et al. |
| 7,541,169 B2 | 6/2009 | Freimuth et al. |
| 7,598,052 B2 | 10/2009 | Giordano et al. |
| 7,767,391 B2 | 8/2010 | Scott et al. |
| 7,901,881 B2 | 3/2011 | Libutti et al. |
| 7,901,888 B2 | 3/2011 | Kebebew |
| 7,927,826 B2 | 4/2011 | Riggins et al. |
| 8,008,009 B2 | 8/2011 | Choquet-Kastylevsky et al. |
| 8,202,692 B2 | 6/2012 | Giordano et al. |
| 8,293,880 B2 | 10/2012 | Cote et al. |
| 8,354,228 B2 | 1/2013 | Ron |
| 8,465,914 B2 | 6/2013 | Brown et al. |
| 8,568,971 B2 | 10/2013 | Brown et al. |
| 8,802,599 B2 | 8/2014 | Aharonov et al. |
| 8,828,656 B2 | 9/2014 | Bullerdiek et al. |
| 8,877,445 B2 | 11/2014 | Shackney |
| 8,945,829 B2 | 2/2015 | Keutgen et al. |
| 9,040,286 B2 | 5/2015 | Zon et al. |
| 9,096,906 B2 | 8/2015 | Aharonov et al. |
| 9,157,123 B2 | 10/2015 | Xing |
| 9,175,352 B2 | 11/2015 | Keutgen et al. |
| 9,234,244 B2 | 1/2016 | Zeiger et al. |
| 9,587,279 B2 | 3/2017 | Fahey, III et al. |
| 9,708,667 B2 | 7/2017 | Yanai et al. |
| 9,920,374 B2 | 3/2018 | Brody et al. |
| 2002/0081612 A1 | 6/2002 | Katz et al. |
| 2002/0094547 A1 | 7/2002 | Burstein |
| 2002/0160388 A1 | 10/2002 | Macina et al. |
| 2003/0104499 A1 | 6/2003 | Pressman et al. |
| 2004/0005294 A1 | 1/2004 | Lee |
| 2004/0009489 A1 | 1/2004 | Golub et al. |
| 2004/0063120 A1 | 4/2004 | Beer et al. |
| 2004/0197785 A1 | 10/2004 | Willey et al. |
| 2004/0241725 A1 | 12/2004 | Xiao et al. |
| 2004/0241728 A1 | 12/2004 | Liew |
| 2005/0260586 A1 | 11/2005 | Demuth et al. |
| 2005/0266409 A1 | 12/2005 | Brown et al. |
| 2006/0003171 A1 | 1/2006 | Igawa et al. |
| 2006/0019272 A1 | 1/2006 | Geraci et al. |
| 2006/0127928 A1 | 6/2006 | Bacus et al. |
| 2006/0154278 A1 | 7/2006 | Brody et al. |
| 2006/0183144 A1 | 8/2006 | Willey et al. |
| 2006/0188909 A1 | 8/2006 | Willey et al. |
| 2006/0190192 A1 | 8/2006 | Willey et al. |
| 2006/0194216 A1 | 8/2006 | Willey et al. |
| 2006/0241869 A1 | 10/2006 | Schadt et al. |
| 2006/0252057 A1 | 11/2006 | Raponi et al. |
| 2007/0092891 A1 | 4/2007 | Willey et al. |
| 2007/0092892 A1 | 4/2007 | Willey et al. |
| 2007/0092893 A1 | 4/2007 | Willey et al. |
| 2007/0148650 A1 | 6/2007 | Brody et al. |
| 2008/0254470 A1 | 10/2008 | Berlin |
| 2009/0029477 A1 | 1/2009 | Meller et al. |
| 2009/0061454 A1 | 3/2009 | Brody et al. |
| 2009/0186951 A1 | 7/2009 | Brody et al. |
| 2009/0246779 A1 | 10/2009 | Rabinovitch et al. |
| 2009/0291853 A1 | 11/2009 | Kim et al. |
| 2009/0311692 A1 | 12/2009 | Brody et al. |
| 2010/0035244 A1 | 2/2010 | Brody et al. |
| 2010/0055689 A1 | 3/2010 | Spira et al. |
| 2010/0119474 A1* | 5/2010 | Crystal .............. C12Q 1/6883 424/85.2 |
| 2010/0204058 A1 | 8/2010 | Chang et al. |
| 2010/0255486 A1 | 10/2010 | Showe et al. |
| 2011/0053158 A1 | 3/2011 | Mambo et al. |
| 2011/0190150 A1 | 8/2011 | Brody et al. |
| 2011/0190156 A1 | 8/2011 | Whitfield et al. |
| 2011/0217717 A1* | 9/2011 | Brody .................. C12Q 1/6886 435/6.14 |
| 2011/0224313 A1 | 9/2011 | Tsao et al. |
| 2011/0294684 A1 | 12/2011 | Baty et al. |
| 2011/0312520 A1 | 12/2011 | Kennedy et al. |
| 2012/0041686 A1 | 2/2012 | Brody et al. |
| 2012/0122718 A1 | 5/2012 | Reisman |
| 2012/0157334 A1 | 6/2012 | Beaudenon-Huibregtse et al. |
| 2012/0190567 A1 | 7/2012 | Brody et al. |
| 2012/0214165 A1 | 8/2012 | Walfish et al. |
| 2012/0264626 A1 | 10/2012 | Nana-Sinkam et al. |
| 2012/0288860 A1 | 11/2012 | Van Hoek et al. |
| 2012/0322673 A1 | 12/2012 | Brody et al. |
| 2012/0329666 A1 | 12/2012 | Steele et al. |
| 2013/0023437 A1 | 1/2013 | Brody et al. |
| 2013/0029873 A1 | 1/2013 | De Perrot et al. |
| 2013/0142728 A1 | 6/2013 | Beaudenon-Huibregtse et al. |
| 2013/0196868 A1 | 8/2013 | Lebowitz et al. |
| 2013/0303826 A1 | 11/2013 | Jurisica et al. |
| 2014/0121126 A1 | 5/2014 | Bivona et al. |
| 2014/0179771 A1 | 6/2014 | Bancel et al. |
| 2014/0220006 A1 | 8/2014 | Aghvanyan et al. |
| 2014/0243240 A1 | 8/2014 | Soldin et al. |
| 2014/0315199 A1 | 10/2014 | Rhodes et al. |
| 2014/0315739 A1 | 10/2014 | Aharonov et al. |
| 2014/0329251 A1 | 11/2014 | Moerman et al. |
| 2014/0349856 A1 | 11/2014 | Schnabel et al. |
| 2014/0378425 A1 | 12/2014 | Wilde et al. |
| 2015/0038376 A1 | 2/2015 | Tian et al. |
| 2015/0080243 A1 | 3/2015 | Whitney et al. |
| 2015/0088430 A1 | 3/2015 | Whitney et al. |
| 2015/0099665 A1 | 4/2015 | Rosenfeld et al. |
| 2015/0141470 A1 | 5/2015 | Garraway et al. |
| 2015/0152474 A1 | 6/2015 | Pawlowski et al. |
| 2015/0232945 A1 | 8/2015 | Brody et al. |
| 2015/0275306 A1 | 10/2015 | Bernards et al. |
| 2015/0299808 A1 | 10/2015 | Gonzalez et al. |
| 2015/0307947 A1 | 10/2015 | Basu et al. |
| 2015/0337385 A1 | 11/2015 | Harris et al. |
| 2015/0368724 A1 | 12/2015 | Aharonov et al. |
| 2016/0024586 A1 | 1/2016 | Delfour et al. |
| 2016/0032400 A1 | 2/2016 | Gomis et al. |
| 2016/0115546 A1 | 4/2016 | Rosenfeld et al. |
| 2016/0120832 A1 | 5/2016 | Rabinowitz et al. |
| 2016/0130656 A1 | 5/2016 | Whitney et al. |
| 2017/0127976 A1 | 5/2017 | Phillips et al. |
| 2017/0166980 A1 | 6/2017 | Fahey, III et al. |
| 2017/0226591 A1 | 8/2017 | Brody et al. |
| 2017/0247759 A1 | 8/2017 | Wilde et al. |
| 2017/0328908 A1 | 11/2017 | Brody et al. |
| 2017/0335396 A1 | 11/2017 | Kennedy et al. |
| 2018/0171418 A1 | 6/2018 | Brody et al. |

FOREIGN PATENT DOCUMENTS

| | | | |
|---|---|---|---|
| EP | 1403638 A1 | 3/2004 |
| JP | 2015519966 A | 7/2015 |
| WO | WO-9960160 A1 | 11/1999 |
| WO | WO-0006780 A1 | 2/2000 |
| WO | WO-0128428 A1 | 4/2001 |
| WO | WO-0206791 A2 | 1/2002 |
| WO | WO-0244331 A2 | 6/2002 |
| WO | WO-02072866 A2 | 9/2002 |
| WO | WO-02086443 A2 | 10/2002 |
| WO | WO-03015613 A2 | 2/2003 |
| WO | WO-03029273 A2 | 4/2003 |
| WO | WO-03040325 A2 | 5/2003 |

(56) References Cited

FOREIGN PATENT DOCUMENTS

| | | |
|---|---|---|
| WO | WO-2004005891 A2 | 1/2004 |
| WO | WO-2004029055 A1 | 4/2004 |
| WO | WO-2004091511 A2 | 10/2004 |
| WO | WO-2004111197 A2 | 12/2004 |
| WO | WO-2005000098 A2 | 1/2005 |
| WO | WO-2005047451 A2 | 5/2005 |
| WO | WO-2006105252 A2 | 10/2006 |
| WO | WO-2006113467 A2 | 10/2006 |
| WO | WO-2006113467 A3 | 4/2007 |
| WO | WO-2007103541 A2 | 9/2007 |
| WO | WO-2009006323 A2 | 1/2009 |
| WO | WO-2009039457 A1 | 3/2009 |
| WO | WO-2009121070 A1 | 10/2009 |
| WO | WO-2010054233 A1 | 5/2010 |
| WO | WO-2010056374 A2 | 5/2010 |
| WO | WO-2011086174 A2 | 7/2011 |
| WO | WO-2011094345 A1 | 8/2011 |
| WO | WO-2012006632 A2 | 1/2012 |
| WO | WO-2012129237 A2 | 9/2012 |
| WO | WO-2013033640 A1 | 3/2013 |
| WO | WO-2013049152 A2 | 4/2013 |
| WO | WO-2013163568 A2 | 10/2013 |
| WO | WO-2013177060 A2 | 11/2013 |
| WO | WO-2013190092 A1 | 12/2013 |
| WO | WO-2014144564 A2 | 9/2014 |
| WO | WO-2014186036 A1 | 11/2014 |
| WO | WO-2015068157 A1 | 5/2015 |
| WO | WO-2016011068 A1 | 1/2016 |
| WO | WO-2016073768 A1 | 5/2016 |
| WO | WO-2017197335 A1 | 11/2017 |
| WO | WO-2018009915 A1 | 1/2018 |
| WO | WO-2018048960 A1 | 3/2018 |

OTHER PUBLICATIONS

Huang, Y-T. et al. Journal of Clinical Oncology 27(16):2660 (Jun. 2009).*

Lee, M. et al. Mol. Biol. Rep. 38:5211 (Jan. 2011).*

International Search Report dated Aug. 28, 2014 for International PCT Patent Application No. PCT/US2014/025715.

Abrahamson et al. Cystatins. Biochem. Soc. Symp. 70: 179-199 (2003).

Akashi et al. Histopathologic analysis of sixteen autopsy cases of chronic hypersensitivity pneumonitis and comparison with idiopathic pulmonary fibrosis/usual interstitial pneumonia. American Journal of Clinical Pathology (2009); 131.3: 405-415.

Akita, et al. Molecular Biology of Lung Cancer. The Journal of the Japanese Respiratory Society, 42(5): (2004).

Alexander et al. Preoperative diagnosis of benign thyroid nodules with indeterminate cytology. N Engl J Med. Aug. 23, 2012;367(8):705-15.

Ambion, Inc. GeneAssist Pathway Atlas for P13K Signaling. Accessed from < http://www5.appliedbiosystems.com/tools/pathway/pathway proteins.php?pathway=P13K > on May 3, 2011.

American Thoracic Society, American Thoracic Society/European Respiratory Society International Multidisciplinary Consensus Classification of the Idiopathic Interstitial Pneumonias. Am. J. Respir. Crit. Care Med. 165, 277-304, 2002.

American Thoracic Society. European Respiratory Society. Idiopathic pulmonary fibrosis: diagnosis and treatment. International consensus statement. Am J Respir Crit Care Med (2000); 161.2 pt 1: 646-664.

Anbazhagan et al. Classification of Small Cell Lung Cancer and Pulmonary Carcinoid by Gene Expression Profiles. Cancer Research, 59:5119-5122, (Oct. 15, 1999).

Anders et al. HTSeq—a Python framework to work with high-throughput sequencing data. Bioinformatics (2015); 31(2): 166-169.

Anderson et al. Deaths: Leading Causes for 2001. National Vital Statistics Report; 52(9): 1-88 (Nov. 7, 2003).

Anthonisen et al. Effects of Smoking Intervention and the Use of an Inhaled Anticholinergic Bronchodilator on the Rate of Decline of FEV1. JAMA; 272(19):1497-1505 (Nov. 16, 1994).

Appleby et al. New technologies for ultra-high throughput genotyping in plants. Plant Genomics: Methods and Protocols (2009); 513: 19-39.

Arimura et al. Elevated Serum 6-Defensins Concentrations in Patients with Lung Cancer. Anticancer Res. Nov.-Dec. 2004;24(6):4051-7.

"Bach, et al. Benefits and harms of CT screening for lung cancer: a systematic review. Jama 307.22 (2012): 2418-2429."

Baker, Stuart. The Central Role of Receiver Operating Characteristic (ROC) Curves in Evaluating Tests for the Early Detection of Cancer. Journal of the National Cancer Institute, 95(7): 511-515 (Apr. 2003).

Bauer et al. A novel genomic signature with translational significance for human idiopathic pulmonary fibrosis. American Journal of Respiratory Cell and Molecular Biology (2015); 52.2: 217-231.

Beane et al. A Prediction Model for Lung Cancer Diagnosis that Integrates Genomic and Clinical Features. Cancer Prevention Research, 1:56-64 (2008).

Beane et al. Reversible and permanent effects of tobacco smoke exposure on airway epithelial gene expression. Genome Biology 2007, 8:R201 (Sep. 25, 2007).

Beane-Ebel. Single-Cell RNA Sequencing of the Bronchial Epithelium in Smokers With Lung Cancer. U.S. Army Medical Research and Material Command. Jul. 2015 version. [retrieved on Sep. 19, 2017]. Retrieved from the Internet at http://www.dtic.mil/dtic/tr/fulltext/u2/a624219.pdf.

Beer et al. Gene-expression profiles predict survival of patients with lung adenocarcinoma. Nature Medicine, 8: 816-824 (2002).

Belinksky et al. Aberrant promoter methylation in bronchial epithelium and sputum from current and former smokers. Cancer Res., 62(8): 2370-7 (2002).

Belyavsky et al. PCR-based cDNA library construction: general cDNA libraries at the level of a few cells. Nucleic Acids Research (1989); 17.8: 2919-2932.

Benner, et al. Evolution, language and analogy in functional genomics. Trends in Genetics, 17:414-418 (2001).

Berbescu et al. Transbronchial biopsy in usual interstitial pneumonia. CHEST Journal (May 2006); 129.5: 1126-1131.

Berman, Jeffrey S. Abstract Immunopathology of the nasal mucosa in sarcoidosis National Institutes of Health Grant No. 1 R21 HL077498-01 (Funding Start Date Sep. 15, 2004).

Bernard et al. Multiplex messenger assay: simultaneous, quantitative measurement of expression of many genes in the context of T cell activation. Nucleic Acids Research (1996); 24.8: 1435-1442.

Beum et al. Epidermal Growth Factor Downregulates Core 2 Enzymes in a Human Airway Adenocarcinoma Cell Line. Am. J. Respir. Cell Mol. Biol., 29:48-56 (Jan. 2003).

Bhattacharjee et al. Classification of human lung carcinoma by mRNA expression profiling reveals distinct adenocarcinoma subclasses. Proc Natl Acad Sci USA, 98(24): 13790-5 (Nov. 20, 2001).

Bild et al. Oncogenic Pathway Signatures in Human Cancers as a Guide to Targeted Therapies. Nature, 439: 353-357 (Jan. 2006).

Bjoraker et al. Prognostic significance of histopathologic subsets in idiopathic pulmonary fibrosis. American Journal of Respiratory and Critical Care Medicine (1998); 157.1: 199-203.

Bohula et al. The Efficacy of Small Interfering RNAs Targeted to the Type 1 Insulin-like Growth Factor Receptor (IGF1R) Is Influenced by Secondary Structure in the IGF1R Transcript. The Journal of Biological Chemistry 278(18): 15991-15997 (May 2003).

Bolstad, et al. A comparison of normalization methods for high density oligonucleotide array data based on variance and bias. Bioinformatics. Jan. 22, 2003;19(2):185-93.

Bosse et al. Molecular signature of smoking in human lung tissues. Cancer Research (2012); 72.15: 3753-3763.

Braakhuis et al. A Genetic Explanation of Slaughter's Concept of Field Cancerization Evidence and Clinical Implications. Cancer Research, 63: 1727-1730 (Apr. 2003).

Brambilla et al. p53 Mutant Immunophenotype and Deregulation of p53 Transcription Pathway (Bc12, Bax and Waf1) in Precursor Bronchial Lesions of Lunch Cancer. Clinical Cancer Research (4): 1609-1618 (1998).

(56) References Cited

OTHER PUBLICATIONS

Brody, Jerome S. Abstract: Airway epithelial gene expression in COPD. National Institutes of Health. Grant No. 1RO1HL071771-01 (Funding Start Date Sep. 30, 2002).
Buckanovich et al. Nova, the paraneoplastic Ri antigen, is homologous to an RNA-binding protein and is specifically expressed in the developing motor system. Neuron (1993); 11.4: 657-672.
Camus et al. Interstitial lung disease induced by drugs and radiation. Respiration. Jul.-Aug. 2004;71(4):301-26.
Chan et al. Integrating Transcriptomics and Proteomics . Genomics & Proteomics Magazine, 6(3), text of article reprinted and accessed from http://www.dddmag.com Published Oct. 4, 2007. http://www.dddmag.com.
Chari et al. Effect of active smoking on the human bronchial epithelium transcriptome. BMC Genomics, 8:297 (Aug. 29, 2007).
Chaudhuri et al. Low sputum MMP-9/TIMP ratio is associated with airway narrowing in smokers with asthma. European Respiratory Journal (Jul. 3, 2014); 44(4): 895-904.
Chen et al. Discordant Protein and mRNA Expression in Lung Adenocarcinomas. Molecular and Cellular Proteomics, 1: 304-313 (2001).
Chen et al. Enrichr: interactive and collaborative HTML5 gene list enrichment analysis tool. BMC Bioinformatics (2013); 14: 128.
Chen et al. Up-regulations of Tumor Interleukin-8 Expression by Infiltrating Macrophages: Its Correlation with Tumor Angiogenesis and Patient Survival in Non-Small Cell Lung Cancer. Clinical Cancer Research: p. 729, (Feb. 1, 2003).
Cheng et al. Reduced expression levels of nucleotide excision repair genes in lung cancer: a case-control analysis. Carcinogenesis. 21(8):1527-1530 (2000).
Cheung et al. Natural variation in human gene expression assessed in lymphoblastiod cells. Nature Genetics, 33: 422-425 (Mar. 2003).
Clark et al. Altered Protein Kinase C (PKC) Isoforms in Non-Small Cell Lung Cancer Cells: PKCdelta Promotes Cellular Survival and Chemotherapeutic Resistance. Cancer Research, 63(4): 780-786 (2003).
Coleman et al. Of mouse and man—what is the value of the mouse in predicting gene expression in humans? Drug Discov Today 8(6) (Mar. 2003): 233-235.
Collard et al. Changes in clinical and physiologic variables predict survival in idiopathic pulmonary fibrosis. American Journal of Respiratory and Critical Care Medicine (May 2003); 168.5: 538-542.
Cooper. Gene Expression Studies in Lung Cancer. The Molecular Genetics of Lung Cancer, pp. 167-186, (2005).
Cortes et al. Support-vector networks. Machine Learning. 1995; 20:273-297.
Cottin et al. Neglected evidence in idiopathic pulmonary fibrosis and the importance of early diagnosis and treatment. European Respiratory Review (Mar. 1, 2014); 23.131: 106-110.
Covey et al. Factors associated with pneumothorax and pneumothorax requiring treatment after percutaneous lung biopsy in 443 consecutive patients. Journal of Vascular and Interventional Radiology (2004); 15.5: 479-483.
Crawford et al. Normal Bronchial Epithelial Cell Expression of Glutathione Transferase P1, Glutathione Transferase M3, and Glutathione Peroxidase is Low in Subjects with Bronchogenic Carcinoma. Cancer Research, 60: 1609-1618 (Mar. 15, 2000).
Cummings, SR. et al. Estimating the probability of malignancy in solitary pulmonary nodules. A Bayesian approach, Am Rev Respir Dis 1986;134:449-52 (1986).
Dai et al. Evolving gene/transcript definitions significantly alter the interpretation of GeneChip data. Nucleic Acids Research 33.20 (2005): e175-e175.
Danel et al. Quantitative Assessment of the Epithelial and Inflammatory Cell Populations in Large Airways of Normals and Individuals with Cystic Fibrosis. Am. Journal of Resp. and Critical Care Medicine 153:362-368 (1996).
Dauletbaev et al. Expression of Human Beta Defensin (HBD-1 and HBD-2) mRNA in Nasal Epithelia of Adult Cystic Fibrosis Patients, Healthy Individuals, and Individuals with Acute Cold. Respiration, 69:46-51 (2002).
DeLong et al. Comparing the areas under two or more correlated receiver operating characteristic curves: a nonparametric approach. Biometrics (1988); 44(3): 837-845.
DeLuca et al. RNA-SeQC: RNA-seq metrics for quality control and process optimization. Bioinformatics (2012); 28.11: 1530-1532.
DeMeo et al. The SERPINE2 gene is associated with chronic obstructive pulmonary disease. Am J Hum Genet., 78(2): 253-264 (Feb. 2006).
Demoly et al. c-fos Proto-oncogene Expression in Bronchial Biopsies of Asthmatics. American Journal of Respiratory Cell and Molecular Biology 7:128-133 (1992).
Dempsey, et al. Lung disease and PKCs. Pharmacol Res., 55 6 : 545-59 2007.
DeMuth et al. The Gene Expression of Index c-myc X E2F-1/p21 Is Highly Predictive of Malignant Phenotype in Human Bronchial Epithelial Cells. Am. J. Cell Mol. Bio. (19): 18-24 (1998).
Deng et al. Ubiquitous Induction of Resistance to Platinum Drugs in Human Ovarian, Cervical, Germ-Cell and Lung Carcinoma Tumor Cells Overexpressing Isoforms 1 and 2 of Dihydrodiol Dehydrogenase. Cancer Chemother. PharmacoL, 54:301-307, (2004).
Denis et al. RING3 Kinase Transactivates Promoters of Cell Cycle Regulatory Genes through E2F1 Cell. Growth Differ; 11: 417-424 (Aug. 2000).
Depeursinge et al. Automated classification of usual interstitial pneumonia using regional volumetric texture analysis in high-resolution computed tomography. Invest Radiol. Apr. 2015;50(4):261-7.
DePianto et al. Heterogeneous gene expression signatures correspond to distinct lung pathologies and biomarkers of disease severity in idiopathic pulmonary fibrosis. Thorax (2015); 70.1: 48-56.
Details for HG-U133A:217291 _AT (CEACAMS) (https://www.affymetrix.com/analysis/netaffx/fullrecord.affx?pk=HG-U133A:217291 _AT, downloaded Apr. 22, 2016).
Details for HG-U112A:823_AT (http://www.affymetrix.com/analysis/netaffx/fullrecord.affx?pk=HG-U133A:823 AT, downloaded Dec. 10, 2012).
Details for HG-U133A:202831_AT (https://www.affymetrix.com/analysis/netaffx/fullrecord.affx?pk=HG-U133A:202831 AT, downloaded Dec. 10, 2012).
Details for HG-U133a-207469_S_AT (https://www.affymetrix.com/analysis/netaffx/fullrecod.affx?pk=HG-U133A:207469 S AT, downloaded Dec. 10, 2012).
Details for HG-U133A:210519_S_AT (https://www.affvmetrix.com/analysis/netaffx/fullrecord.affx?pk=HG-U133A:210519 S AT downloaded Dec. 10, 2012).
Detterbeck et al. Screening for lung cancer: diagnosis and management of lung cancer: American College of Chest Physicians evidence-based clinical practice guidelines. CHEST Journal (2013); 143.5_suppl: e78S-e92S.
Ding et al. A high-throughput gene expression analysis technique using competitive PCR and matrix-assisted laser desorption ionization time-of-flight MS. Proceedings of the National Academy of Sciences USA (Mar. 2003); 100.6: 3059-3064.
Dobin, et al., Star: Ultrafast Universal RNA-Seq Aligner, Bioinformatics, Oct. 25, 2012, 29:15-21.
Doll et al. Mortality in relation to smoking: 40 years' observations on male British doctors. BMJ; 309:901-911 (Oct. 8, 1994).
Doris et al. Quantitative analysis of gene expression by ion-pair high-performance liquid chromatography. Journal of Chromatography A (1998); 806.1: 47-60.
Du Bois et al. Ascertainment of individual risk of mortality for patients with idiopathic pulmonary fibrosis. American Journal of Respiratory and Critical Care Medicine (2011); 184.4: 459-466.
Du Bois, R. M. Strategies for treating idiopathic pulmonary fibrosis. Nature reviews Drug Discovery (2010); 9.2: 129-140.
Durham et al. The Relationship Between COPD and Lung Cancer. Lung Cancer, 90:121-127, (2015).

(56) References Cited

OTHER PUBLICATIONS

Ebbert, et al. Lung Cancer Risk Reduction After Smoking Cessation: Observations From a Prospective Cohort of Women. J Clin Oncol; 21(5):921-926 (Mar. 1, 2003).
Enard et al. Intra- and Interspecific Variation in Primate Gene Expression Patterns. Science 296: 340-343 (2002).
EP14797859.7 Extended Search Report dated Oct. 19, 2016.
Ernst et al. Interventional pulmonary procedures: guidelines from the American College of Chest Physicians. CHEST Journal (May 2003); 123.5: 1693-1717.
Fahy, JV. Remodeling of the Airway Epithelium in Asthma. Am. J. Respir. Crit. Care Med. 164:S46-S51 (2001).
Fielding et al. Heterogeneous Nuclear Ribonucleoprotein A2B1 Up-Regulation in Bronchial Lavage Specimens: A Clinical Marker of Early Lung Cancer Detection. Clinical Cancer Research. 5:4048-4052 (1999).
Flaherty et al. Clinical significance of histological classification of idiopathic interstitial pneumonia. European Respiratory Journal (2002); 19.2: 275-283.
Flaherty et al. Histopathologic variability in usual and nonspecific interstitial pneumonias. American Journal of Respiratory and Critical Care Medicine (2001); 164.9: 1722-1727.
Flaherty et al. Idiopathic interstitial pneumonia: what is the effect of a multidisciplinary approach to diagnosis?. American Journal of Respiratory and Critical Care Medicine (2004); 170.8: 904-910.
Flaherty et al. Radiological versus histological diagnosis in UIP and NSIP: survival implications. Thorax (Feb. 2003); 58.2: 143-148.
Fontaine-Delaruelle et al. Is transthoracic core needle biopsy under CT scan a good deal for benign diseases' diagnosis? European Respiratory Journal (2014); 44.Suppl 58: p. 679.
Fox et al. Applications of ultra-high-throughput sequencing. (ed. Belostotsky, D.A., Plant Systems Biology (2009); 5: 79-108.
Franklin, et al. Widely Dispersed p53 Mutation in Respiratory Epithelium. The Journal of Clinical Investigation, 100(8): 2133-2137 (1997).
Freeman et al. DNA from Buccal Swabs Recruited by Mail: Evaluation of Storage Effects on Long-term Stability and Suitability for Multiplex Polymerase Chain Reaction Genotyping, Behavior Genetics, 33: 67 (2003).
Friedman et al. Regularization Paths for Generalized Linear Models via Coordinate Descent. J Stat Softw 33:1-22 (2010).
Fritz et al. Nasal mucosal gene expression in patients with allergic rhinitis with and without nasal polyps. Journal of Allergy Clin. Immunol, 112(6): 1057-1063 (Dec. 2003).
Frohman et al. Rapid production of full-length cDNAs from rare transcripts: amplification using a single gene-specific oligonucleotide primer. Proc Natl Acad Sci U S A. Dec. 1988;85(23):8998-9002.
Fukumoto et al. Overexpression of the Aldo-Keto Reductase Family Protein AKR1B10 is Highly Correlated with Smokers' Non-Small Cell Lung Carcinomas. Clinical Cancer Research 11:1776-1785 (2005).
Furneaux et al. Selective expression of Purkinje-cell antigens in tumor tissue from patients with paraneoplastic cerebellar degeneration. New England Journal of Medicine (1990); 322.26: 1844-1851.
Garber et al. Diversity of gene expression in adenocarcinoma of the lung. PNAS, 98(24): 13784-13789 (Nov. 20, 2001).
Garcia-Alvarez et al. Tissue inhibitor of metalloproteinase-3 is up-regulated by transforming growth factor-131 in vitro and expressed in fibroblastic foci in vivo in idiopathic pulmonary fibrosis. Experimental Lung Research (Apr. 2006); 32(5): 201-214.
Garcia-Closas et al. Collection of Genomic DNA from Adults in Epidemiological Studies by Buccal Cytobrush and Mouthwash. Cancer Epidemiology, Biomarkers and Prevention, 10(6): 687-696 (2001).
Gebel, et al. Gene expression profiling in respiratory tissues from rats exposed to mainstream cigarette smoke. Carcinogenesis. Feb. 2004;25(2):169-78.
Geraghty et al. CT-guided transthoracic needle aspiration biopsy of pulmonary nodules: Needle size and pneumothorax rate 1. Radiology. Nov. 2003;229(2):475-81.
Gildea et al. Electromagnetic navigation diagnostic bronchoscopy: a prospective study. American Journal of Respiratory and Critical Care Medicine. Nov. 2006; 174(9):982-989.
Golub, et al. Molecular classification of cancer: Discovery and class prediction by gene expression monitoring. Science, 286, 531-537, 1999.
Gould et al. A clinical model to estimate the pretest probability of lung cancer in patients with solitary pulmonary nodules. CHEST Journal (2007); 131.2: 383-388.
Gould et al. Evaluation of individuals with pulmonary nodules: When is it lung cancer?: Diagnosis and management of lung cancer: American College of Chest Physicians evidence-based clinical practice guidelines. CHEST Journal (2013); 143.5_suppl: e935-e1205.
Gould et al. Recent trends in the identification of incidental pulmonary nodules. Am J Respir Crit Care Med. Nov. 15, 2015;192(10):1208-14.
Greenlee et al. Cancer Statistics, 2001. CA Cancer J Clin; 51(1):15-36 (2001).
Grepmeier et al. Deletions at chromosome 2q and 12p are early frequent molecular alterations in bronchial epithelium and NSCLC of long-term smokers. Int J Oncol., 27(2):481-8(2005).
Grogan et al. Thoracic operations for pulmonary nodules are frequently not futile in patients with benign disease. Journal of Thoracic Oncology (2011); 6.10: 1720-1725.
Guajardo et al. Altered gene expression profiles in nasal respiratory epithelium reflect stable versus actue childhood asthma. J. Allergy Clin Immunol; 115(2): 243-251 (2005).
Guatelli et al. Isothermal, in vitro amplification of nucleic acids by a multienzyme reaction modeled after retroviral replication. PNAS USA 87(5):1874-1878 (1990).
Gulati, Mridu. Diagnostic assessment of patients with interstitial lung disease. Prim Care Respir J. Jun. 2011;20(2):120-7.
Gurney, JW. Determining the likelihood of malignancy in solitary pulmonary nodules with Bayesian analysis Part 1 Theory. Radiology 1993;186:405-13 (2005).
Gustafson et al. Airway P13K Pathway Activation Is an Early and Reversible Even in Lung Cancer Development. < www.sciencetransmlationmedicine.org >. 2(26) (2010). </www.sciencetransmlationmedicine.org >.
Hackett et al. Variability of antioxidant-related gene expression in the airway epithelium of cigarette smokers. Am J Respir Cell Mol Biol., 29: 331-43 (Apr. 2003).
Hamilton et al. Diagnosis of lung cancer in primary care: a structured review. Fam Pract. Dec. 2004;21(6):605-11.
Hanley et al. The meaning and use of the area under a receiver operating characteristic (ROC) curve. Radiology. Apr. 1982;143(1):29-36.
Hecht, SS. Tobacco carcinogens, their biomarkers and tobacco-induced cancer. Nature Review Cancer; 3:733-744 (Oct. 2003).
Hellmann et al. Gene Profiling of Cultured Human Bronchia Epithelial and Lung Cacinoma Cells. Toxicological Sciences, 61: 154-163 (2001).
Hennessy et al. Exploiting the PI3KAKT Pathway for Cancer Drug Discovery Nature vol. 4:988-1004 (2005).
Hirsch et al. Early Detection of Lung Cancer: Clinical Perspectives of Recent Advances in Biology and Radiology. Clinical Cancer Research (7): 5-22 (2001).
Hodnett et al. Fibrosing interstitial lung disease: a practical HRCT based approach to diagnosis and management and review of the literature. Am J Respir Crit Care Med (2013); 188.2: 141-149.
Holland, et al., Detection of specific polymerase chain reaction product by utilizing the 5' to 3' exonuclease activity of Thermus aquaticus DNA polymerase. PNAS (USA) 88:7276-7280, 1991.
Hoshikawa, et al. Hypoxia induces different genes in the lungs of rats compared with mice. Physiol Genomics. Feb. 6, 2003;12(3):209-19.
Howlader et al. SEER stat fact sheets: lung and bronchus cancer. Bethesda: National Cancer Institute (2011). http://seer.cancer.gov/statfacts/html/lungb.html [Downloaded Oct. 18, 2016], 9 pages.

(56) References Cited

OTHER PUBLICATIONS

Huang et al. Systematic and integrative analysis of large gene lists using DAVID bioinformatics resources. Nature protocols 4:44-57 (2009).
Hummert et al. Creation and Comparison of Different Chip Definition Files for Affymetrix Microarrays. Proceedings of the International Conference on Bioinformatics and Computational Biology. BioComp'11, Jul. 18-21, 2011, Las Vegas, USA, 1(1): 16-22.
Ikeda et al. Malignancy associated changes in bronchial epithelial cells and clinical application as a biomarker. Lung Cancer, 19(3): 161-166 (1998).
Imelfort et al. De novo sequencing of plant genomes using second-generation technologies. Briefings in Bioinformatics (2009); 10.6: 609-618.
Irizarry, et al. Exploration, normalization, and summaries of high density oligonucleotide array probe level data. Biostatistics. Apr. 2003;4(2):249-64.
Irizarry et al. Summaries of Affymetrix GeneChip probe level data. Nucleic Acids Res 31(4):e15 (Feb. 2003).
Ivana et al. Expression of cilium-associated genes defines novel molecular subtypes of idiopathic pulmonary fibrosis. Thorax(2013): thoraxjnl-2012.
Ivana et al. Gene expression profiling of familial and sporadic interstitial pneumonia. American journal of respiratory and critical care medicine 175.1 (2007): 45-54.
Jang et al. Activation of melanoma antigen tumor antigens occurs early in lung carcinogenesis. Cancer Research 61: 7959-7963 (2001).
Johnson et al. Adjusting batch effects in microarray expression data using empirical Bayes methods. Biostatistics (2007); 8.1: 118-127.
Jonigk et al. Molecular profiling in lung biopsies of human pulmonary allografts to predict chronic lung allograft dysfunction. The American Journal of Pathology (2015); 185.12: 3178-3188.
Joshua D Campbell et al: "A gene expression signature of emphysema-related lung destruction and its reversal by the tripeptide GHK",Genome Med, Biomed Central L to, London, UK, vol. 4, No. 8, Aug. 31, 2012 (Aug. 31, 2012 ), p. 67.
Kadara et al. Transcriptomic architecture of the adjacent airway field cancerization in non-small cell lung cancer. Journal of the National Cancer Institute (2014); 106.3: dju004.
Kanner et al. Effects of randomized assignment to a smoking cessation intervention and changes in smoking habits on respiratory symptoms in smokers with early chronic obstructive pulmonary disease: the lung health study. American Journal of Medicine; 106:410-416 (1999).
Kao, et al. Tumor-associated Antigen L6 and the Invasion of Human Lung Cancer Cells. Clin Cancer Res. 9:2807-2816 (Jul. 2003).
Katz et al. Automated detection of genetic abnormalities combined with cytology in sputum is a sensitive predictor of lung cancer. Modern Pathology;21:950-960 (2008).
Katzenstein, Anna-Luise A. Smoking-related interstitial fibrosis (SRIF), pathogenesis and treatment of usual interstitial pneumonia (UIP), and transbronchial biopsy in UIP. Modern Pathology (2012); 25: S68-S78.
Katzenstein et al. Diagnosis of usual interstitial pneumonia and distinction from other fibrosing interstitial lung diseases. Erratum to Diagnosis of usual interstitial pneumonia and distinction from other fibrosing interstitial lung diseases. [Hum Pathol (2008); 39: 1275-1294]. Human Pathology (2008); 39.11: 1562-1581.
Katzenstein et al. Idiopathic Pulmonary Fibrosis. Am J Respir Crit Care Med (1998); 157: 1301-1315.
Katzenstein et al. Usual interstitial pneumonia: histologic study of biopsy and explant specimens. The American Journal of Surgical Pathology (2002); 26.12: 1567-1577.
Kauffmann et al. arrayQualityMetrics—a bioconductor package for quality assessment of microarray data. Bioinformatics (2009); 25.3: 415-416.
Kazemi-Noureini et al. Differential gene expression between squamous cell carcinoma of esophageus and its normal epithelium; altered pattern of mal, akrlc2, and rab11a expression. World J Gastroenterol. Jun. 15, 2004; 10(12): 1716-1721.

Khan et al. Classification and Diagnostic Prediction of Cancers Using Gene Expression Profiling and Artificial Neural Networks. Nature Medicine, 7(6):673-679, (Jun. 2001).
Kim et al. Identification of bronchioalveolar stem cells in normal lung and lung cancer. Cell (2005); 121.6: 823-835.
King et al. Idiopathic pulmonary fibrosis. The Lancet (2011); 378.9807: 1949-1961.
King Jr. et al. A phase 3 trial of pirfenidone in patients with idiopathic pulmonary fibrosis. N Engl J Med. May 29, 2014;370(22):2083-92.
Kiss, et al. Anatomisk Atlas over Manniskokroppen, band II. Natur och Kultur Stockholm, Stockholm, Sweden ISBN: 91-27-67278-6; 1973.
Kitahara et al. Alternations of Gene Expression during Colorectal Carcinogenesis Revealed by cDNA Microarrays after Laser-Capture Microdissection of Tumor Tissues and Normal Epithelia. Cancer Research, 61: 3544-3549 (May 1, 2001).
Knudsen et al. Ri antibodies in patients with breast, ovarian or small cell lung cancer determined by a sensitive immunoprecipitation technique. Cancer Immunology Immunotherapy 55.10 (Jan. 2006): 1280-1284.
Kocarnik et al. Replication of Associations Between GWAS SNPs and Melanoma Risk in the Population Architecture Using Genomics and Epidemiology (PAGE) Study. Journal of Investigative Dermatology, 134:2049-2052, (Feb. 27, 2014).
Kraft et al. Expression of epithelial markers in nocturnal asthma. Journal of Allergy and Clinical Immunology, 102(3): 376-381 (1998).
Kuriakose et al. Selection and validation of differentially expressed genes in head and neck cancer. Cellular and Molecular Life Sciences CMLS 61. (11):1372-83, Jul. 2004.
Kwoh et al. Transcription-based amplification system and detection of amplified human immunodeficiency virus type 1 with a bead-based sandwich hybridization format. PNAS USA 86(4):1173-1177 (1989).
Lacroix et al. Sensitive Detection of Rare Cancer Cell in Sputum and Peripheral Blood Samples of Patients with Lunch Cancer by Preprogrp-Specific TR-PCR. Int. J. Cancer, vol. 92: 1-8 (2001).
Lam et al. A Phase I Study of myo-Inositol for Lung Cancer Chemoprevention. Cancer Epidemiology, Biomarkers & Prevention 15(8): 1526-1531 (Aug. 2006).
Lampe et al. Signatures of environmental exposures using peripheral leukocyte gene expression: tobacco smoke. Cancer Epidemiology Biomarkers & Prevention (2004); 13.3: 445-453.
Landegren, et al., A ligase-mediated gene detection technique. Science. Aug. 26, 1988;241(4869):1077-80.
Lander, et al. Initial sequencing and analysis of the human genome. Nature, 409 (Feb. 15, 2001): 860-921.
Langford et al. Is the Property of Being Positively Correlated Transitive. The American Statistician. 55(4):322-325 (2001).
Lewis et al. Cotinine levels and self-reported smoking status in patients attending a bronchoscopy clinic. Biomarkers (2003); 8.3-4: 218-228.
Li et al. Gene expression profiling in human lung fibroblast following cadmium exposure. Food and Chemical Toxicology (2008); 46.3: 1131-1137.
Li, Lexin. Survival prediction of diffuse large-B-cell lymphoma based on both clinical and gene expression information. Bioinformatics 2006; 22:466-71, (Feb. 2006).
Liao et al. Expression and significance of PTEN/PI3K signal transduction-related proteins in nonsmall cell lung cancer. Ai Zheng 25: 10, p. 1238-42. Abstract (Oct. 2006).
Lin et al. Effects of Dexamethasone on Acute Lung Injury Rat Cells Signal Transduction Systems ERK and PI3-K. Medical Journal of Chinese People's Liberation Army 6(31): 592-594 (Sep. 2006).
Liu et al. An oligonucleotide microchip for genome-wide microRNA profiling in human and mouse tissues. Proc Natl Acad Sci USA, 2004, 101(26):9740-9744.
Liu et al. Effects of physiological versus pharmacological g-carotene supplementation on cell proliferation and histopathological changes in the lungs of cigarette smoke-exposed ferrets. Carcinogenesis, 21: 2245-2253 (2000).

(56) References Cited

OTHER PUBLICATIONS

Liu, et al. Quantitative Proteome Analysis Reveals Annexin A3 as a Novel Biomarker in Lung Adenocarcinoma. Journal of Pathology, 217: 54-64 (2009).
Lockstone et al. Gene set analysis of lung samples provides insight into pathogenesis of progressive, fibrotic pulmonary sarcoidosis. American Journal of Respiratory and Critical Care Medicine (2010); 181.12: 1367-1375.
Love, et al. Moderated estimation of fold change and dispersion for RNA-seq data with DESeq2. Genome Biol. Dec 5, 2014;15(12):550.
MacKay, et al. Targeting the protein kinase C family: are we there yet? Nature Reviews Cancer. 7(7):554-62 (Jul. 1, 2007).
MacMahon et al. Guidelines for management of small pulmonary nodules detected on CT scans: a statement from the Fleischner Society 1. Radiology (2005); 237.2: 395-400.
Mannino et al. Low lung function and incident lung cancer in the United States: data From the First National Health and Nutrition Examination Survey follow-up. Arch Intern Med. 163(12):1475-80 (Jun. 23, 2003).
Margulies, et al. Genome sequencing in microfabricated high-density picolitre reactors. Nature. Sep. 15, 2005;437(7057):376-80. Epub Jul. 31, 2005.
Mariani Thomas J et al: "Molecular markers for quantitative and discrete COPD phenotypes",The FASEB Journal, Federation of American Societies for Experimental Biology, US, vol. 21, No. 5, Apr. 1, 2007 (Apr. 1, 2007), p. A8.
Marinov et al. Targeting mTOR signaling in lung cancer. Critical Reviews in Oncology/Hematology 63: 172-182 (Aug. 2007).
May, Robert M. How Many Species Are There on Earth? Science, 241: 1141-1449 (1988).
McWilliams et al. Probability of cancer in pulmonary nodules detected on first screening CT. New England Journal of Medicine (2013); 369.10: 910-919.
Medical News: Targeted, Oral Agent Enzastaurin Shows Favorable Results in Late-Stage Lung Cancer. (Jun. 11, 2007), Retrieved from the Internet URL: < https://www.medicalnewstoday.com/releases/73761.php.
Memoli et al. Meta-analysis of guided bronchoscopy for the evaluation of the pulmonary nodule. CHEST Journal (2012); 142.2: 385-393.
Merrium-Webster.com (http://www.merriam-webstercom/dictionary/questionnaire), downloaded Oct. 26, 2013.
Meyer et al. Support vector machines. The Interface to libsvm in package e1071. FH Technikum Wien, Austria (2015); pp. 1-8.
Mi, et al., The PANTHER database of protein families, subfamilies, functions and pathways, Neucleic acids research, 2005, 3: D284-88.
Michalczyk et al. Fresh and cultured buccal cells as a source of mRNA and protein for molecular analysis. Biotechniques. Aug. 2004;37(2):262-4, 266-9.
Miklos, et al. Microarray reality checks in the context of a complex disease. Nature Biotechnology, 22:5 (May 2005).
Minhyeok; Lee et al., "Copy Number Variations of Chromosome 17p13.1 Might be Linked to High Risk of Lung Cancer in Heavy Smokers", Mol Biol Rep, 2011, 38, 5211-5217.
Miura et al. Laser capture microdissection and microarray expression analysis of lung adenocarcinoma reveals tobacco smoking- and prognosis-related molecular profiles. Cancer Res., 62(11): 3244-50 (Jun. 1, 2002).
Modrek et al. Genome-wide detection of alternative splicing in expressed sequences of human genes. Nucleic Acids Research, 29(13): 2850-2859 (2001).
Moller et al. Altered Ratio of Endothelin ETA- and ETB Receptor mRNA in Bronchial Biopsies from Patients with Asthma and Chronic Airway Obstruction. (European Journal of Pharmacology, 1999, 365: R1-R3).
Mollerup et al. Sex Differences in Lung CYP1A1 Expression and DNA Adduct Levels among Lung Cancer Patients. Cancer Research, 1999, 59: 3317-3320 (1999).
Mongiat et al. Fibroblast Growth Factor-binding Protein Is a Novel Partner for Perlecan Protein Core. The Journal of Biological Chemistry; 276(13):10263-10271 (Mar. 30, 2001).
Monti et al. Consensus Clustering: A Resampling-Based Method for Class Discovery and Visualization of Gene Expression Microarray Data. Machine Learning (Jul. 2003); 52(1): 91-118.
Morales et al. Accuracy of self-reported tobacco use in newly diagnosed cancer patients. Cancer Causes & Control (2013); 24.6: 1223-1230.
Morin et al., Profiling the HeLa S3 transcriptome using randomly primed cDNA and massively parallel short-read sequencing. Biotechniques, 45:81-94, 2008.
Morozova et al. Applications of next-generation sequencing technologies in functional genomics. Genomics (2008); 92.5: 255-264.
National Lung Screening Trial Research Team et al. Reduced lung-cancer mortality with low-dose computed tomographic screening. N Engl J Med 365:395-409 (2011).
Neubauer et al. Cure of Helicobacter pylori Infection and Duration of Remission of Low-Grade Gastric Mucosa-Associated Lymphoid Tissue Lymphoma. J. Natl. Cancer Inst., 89(18): 1350-1378 (Sep. 17, 1997).
Newton et al. On Differential Variability of Expression Ratios: Improving Statistical Inference about Gene Expression Changes from Microarray Data. Journal of Computational Biology, 8: 37-52 (2001).
Nicholson et al. Inter-observer variation between pathologists in diffuse parenchymal lung disease. Thorax (2004); 59.6: 500-505.
Nicholson et al. The relationship between individual histologic features and disease progression in idiopathic pulmonary fibrosis. American Journal of Respiratory and Critical Care Medicine (2002); 166.2: 173-177.
Nielsen et al. Aquaporins in complex tissues. II. Subcellular distribution in respiratory and glandular tissues of rat. American Journal of Physiology—Cell Physiology (1997); 273.5: C1549-C1561.
Noble et al. Pirfenidone in patients with idiopathic pulmonary fibrosis (CAPACITY): two randomised trials. 2011, Lancet, 377, 1760-69.
Notterman et al. Tumor Biology and Microarray Analysis of Solid Tumors: Colorectal Cancer as a Model System. Microarrays and Cancer Research, Warrington et al (eds.), Eaton Publishing, Westborough, MA, pp. xi-xvi, (2002).
Ohtsuka et al. ADAM28 is overexpressed in human non-small cell lung carcinomas and correlates with cell proliferation and lymph node metastasis. International Journal of Cancer, 118 2 : 263-273, Jan. 2006.
Okudela et al. K-ras Gene Mutation Enhances Motility of Immortalized Airway Cells and Lung Adenocarcinoma Cells Via Akt Activation: Possible Contribution to Non-Invasive Expansion of Lung Adenocarcinoma. Am J Pathol. Jan. 2004; 164(1): 91-100.
Ooi et al. Molecular Profiling of Premalignant Lesions in Lung Squamous Cell Carcinomas Identifies Mechanisms Involved in Stepwise Carcinogenesis. Cancer Prevention Research, 7(5):487-495, (Mar. 11, 2014).
Ost et al. The solitary pulmonary nodule. New England Journal of Medicine (Jun. 19, 2003); 348.25: 2535-2542.
Oster et al. Identification and validation of highly frequent CpG island hypermethylation in colorectal adenomas and carcinomas. International Journal of Cancer (2011); 129.12: 2855-2866.
Otsubo et al. TSPAN2 is involved in cell invasion and motility during lung cancer progression. Cell Reports (2014); 7.2: 527-538.
Pardo et al. Up-regulation and profibrotic role of osteopontin in human idiopathic pulmonary fibrosis. PLoS Med (2005); 2.9: e251.
Peluso et al. Comparison of DNA adduct levels in nasal mucosa, lymphocytes and bronchial mucosa of cigarette smokers and interaction with metabolic gene polymorphisms. Carcinogenesis 25(12): 2459-2465 (2004).
Penning et al. Genomics of smoking exposure and cessation: lessons for cancer prevention and treatment. Cancer Prevention Research (2008); 1.2: 80-83.
Perez et al. Incidence, prevalence, and clinical course of idiopathic pulmonary fibrosis: a population-based study. CHEST Journal (2010); 137.1: 129-137.

(56) References Cited

OTHER PUBLICATIONS

Piotrowski et al. The selected genetic polymorphisms of metalloproteinases MMP2, 7, 9 and MMP inhibitor TIMP2 in sarcoidosis. Medical Science Monitor (2011); 17.10: CR598-CR607.

Pittman et al. Integrated modeling of clinical and gene expression information for personalized prediction of disease outcomes. Proc Natl Acad Sci U S A. Jun. 1, 2004;101(22):8431-6.

Platform GPL6244 https://www.ncbi.nlm.nih.gov/geo/query/acc.cgi?acc=gp16244, Submission Date Dec. 5, 2007 [Downloaded Oct. 18, 2016], 3 pages.

Poletti et al. Invasive diagnostic techniques in idiopathic interstitial pneumonias. Respirology (2016); 21.1: 44-50.

Potti et al. A Genomic Strategy to Refine Prognosis in Early-Stage Non Small-Cell Lung Cancer. The New England Journal of Medicine 2006; 335(6):570-580 (Aug. 2006).

Potti et al. Genomic Signatures to Guide the Use of Chemotherapeutics. Nature Medicine, 12(11): 1294-1300 (Oct. 2006).

Powell et al. Gene expression in lung adenocarcinomas of smokers and nonsmokers. American Journal of Respiratory Cell and Molecular Biology, 29: 157-162 (Aug. 2003).

Powell et al. Patterns of allelic loss differ in lung adenocarcinomas of smokers and nonsmokers. Lung Cancer, 39 1 : 23-29 (2003).

Printout from database NCBIGEO accession No. GSE4115 [Online] NCB dated Feb. 27, 2006.

Proctor, RN. Tobacco and the global lung cancer epidemic. Nature Reviews Cancer, 1: 82-86 (Oct. 2001).

Puissegur et al. miR-210 is overexpressed in late stages of lung cancer and mediates mitochondrial alterations associated with modulation of HIF-1 activity. Cell Death Differ. 18(3):465-478 (2011).

Raghu et al. An official ATS/ERS/JRS/ALAT statement: idiopathic pulmonary fibrosis: evidence-based guidelines for diagnosis and management. American Journal of Respiratory and Critical Care Medicine (2011); 183.6: 788-824.

Reynolds et al. Pre-protachykinin-A mRNA is increased in the airway epithelium of smokers with chronic bronchitis. Respiratory, 6:187-197 (2001).

Richeldi et al. Efficacy and safety of nintedanib in idiopathic pulmonary fibrosis. N Engl J Med. May 29, 2014;370(22):2071-82.

Riise et al. Bronchial Brush Biopsies for Studies of Epithelial Inflammation in Stable Asthma and Nonobstructive Chronic Bronchitis. European Respiratory Journal, 9: 1665-1671 (1996).

Rivera et al. Establishing the diagnosis of lung cancer: Diagnosis and management of lung cancer: American College of Chest Physicians evidence-based clinical practice guidelines. CHEST Journal 143.5_suppl (2013): e142S-e165S.

Robin et al. pROC: an open-source package for R and S+ to analyze and compare ROC curves. BMC Bioinformatics 12:77 (2011).

Ronaghi et al. Real-time DNA sequencing using detection of pyrophosphate release. Anal Biochem. 1996; 242(1):84-89.

Rouskin et al. Genome-wide probing of RNA structure reveals active unfolding of mRNA structures in vivo. Nature. Jan. 30, 2014;505(7485):701-5.

Rusznak et al. Effect of Cigarette Smoke on the Permeability and IL-1B and sICAM-1 Release from Cultured Human Bronchial Epithelial Cells of Never-Smokers, Smokers, and Patients with Chronic Obstructive Pulmonary Disease. Am. J. Respir. Cell Mol. Biol., 23:530536 (2000).

Saal et al. Poor Prognosis in Carcinoma is Associated with a Gene Expression Signature of Aberrant PTEN Tumor Suppressor Pathway Activitiy. PNAS 104(18):7564-7569 (2007).

Saheki et al. Pathogenesis and pathophysiology of citrin (a mitochondrial aspartate glutamate carrier) deficiency. Metabolic Brain Disease; 17(4):335-346 (Dec. 2002).

Saito-Hisaminato et al. Genome-Wide Profiling of Gene Expression in 29 Normal Human Tissues with a cNDA Microarray. DNA Research, 2002, 9:35-45.

Salemi et al. Cerebellar degeneration-related autoantigen 1 (CDR1) gene expression in prostate cancer cell lines. Int J Biol Markers (2013); 29.3: e288-290.

Santiyagu M. Savarimuthu Francis et al: "Genes and Gene Ontologies Common to Airflow Obstruction and Emphysema in the Lungs of Patients with COPD",PLOS ONE, val. 6, No. 3, 2011, p. e17442.

Schembri et al. MicroRNAs as modulators of smoking-induced gene expression changes in human airway epithelium. Proc Natl Acad Sci U S A, 106(71,2319-24 (Feb. 2009).

Schraufangel. "Interstitial Lung Disease," Chapter 10, pp. 99-107, in Breathing in America: Diseases, Progress and Hope, American Thoracic Society (2010).

Schraufnagel, Dean. Breathing in America: Diseases, Progress, and Hope. The American Thoracic Society. Published 2010. 282 pages.

Schulz et al. Activation of bronchial epithelial cells in smokers without airway obstruction and patients with COPD. Chest. May 2004;125(5):1706-13.

Schulz et al. Upregulation of MCAM in primary bronchial epithelial cells from patients with COPD. European Respiratory Journal (Sep. 2003); 22.3: 450-456.

Selman et al. Gene expression profiles distinguish idiopathic pulmonary fibrosis from hypersensitivity pneumonitis. American Journal of Respiratory and Critical Care Medicine (2006); 173.2: 188-198.

Selman et al. Idiopathic pulmonary fibrosis: aberrant recapitulation of developmental programs?. PLoS medicine 5.3 (2008): e62.

Selman et al. Revealing the pathogenic and aging-related mechanisms of the enigmatic idiopathic pulmonary fibrosis. An integral model. Am J Respir Crit Care Med. May 15, 2014;189(10):1161-72.

Shah et al. SIEGE: Smoking Induced Pithelial Gene Expression Database. Nucleic Acids Research, 33: D573-D579 (2005).

Shalon, D. et al. A DNA microarray system for analyzing complex DNA samples using two-color fluorescent probe hybridization. Genome research, 6(7): 639-645 (Jul. 1996).

Shendure et al. Accurate Multiplex Polony Sequencing of an Evolved bacterial Genome. Science (2005) 309:1728-1732.

Shields, PG. Molecular epidemiology of lung cancer. Annals of Oncology, 10(5):57-S11 (1999).

Shin et al. A new Mel-CAM (CD146)-specific monoclonal antibody, MN-4, on paraffin-embedded tissue. Modern Pathology: an Official Journal of the United States and Canadian Academy of Pathology, Inc (1998); 11.11: 1098-1106.

Shim et al. Histopathologic findings of transbronchial biopsy in usual interstitial pneumonia. Pathology International (2010); 60.5: 373-377.

Shriver et al. Sex-Specific Expression of Gastrin-Releasing Peptide Receptor: Relationship to Smoking History and Risk of Lung Cancer. J. Natl. Cancer Inst., 92: 24-33 (2000).

Silvestri et al. A bronchial genomic classifier for the diagnostic evaluation of lung cancer. N Engl J Med. Jul. 16, 2015;373(3):243-51.

Silvestri et al. Latest advances in advanced diagnostic and therapeutic pulmonary procedures. CHEST Journal (2012); 142.6: 1636-1644.

Simon et al. Up-regulation of MUC18 in airway epithelial cells by IL-13: implications in bacterial adherence. American Journal of Respiratory Cell and Molecular Biology (2011); 44.5: 606-613.

Singhal et al. Alterations in cell cycle genes in early stage lung adenocarcinoma identified by expression profiling. Cancer Biol Ther. May-Jun. 2003;2(3):291-8.

Singhal S et al: "Gene expression profiling of Non-small cell lung cancer", Lung Cancer, val. 60, No. 3, Jun. 1, 2008 (Jun. 1, 2008 ), pp. 313-324, XP022690999.

Slonim, Donna. From Patterns to Pathways: Gene Expression Data Analysis Comes of Age. Nature Genetics Supplement, 32: 502-508, 2002.

Smirnov et al. Global gene expression profiling of circulating endothelial cells in patients with metastatic carcinomas. Cancer Res. Mar. 15, 2006;66(6):2918-22.

Smith et al. Prevalence of benign disease in patients undergoing resection for suspected lung cancer. The Annals of Thoracic Surgery (May 2006); 81.5: 1824-1829.

Smyth, Gordon K. Linear models and empirical bayes methods for assessing differential expression in microarray experiments. Stat Appl Genet Mol Biol. 2004;3:Article3. Epub Feb. 12, 2004.

(56) References Cited

OTHER PUBLICATIONS

Soni et al. Progress toward ultrafast DNA sequencing using solid-state nanopores. Clin Chem 53:1996-2001 (2007).

Sotos, et al. The Transitivity Misconception of Pearson's Correlation Coefficient. Statistics Education Research Journal. 8(2):33-55 (2009).

Soumyaroop BhattacharyA1 et al: "Molecular biomarkers for quantitative and discrete COPD phenotypes",American Journal of Respiratory Cell and Molecular Biology, American Lung Association, val. 40, No. 3, (Oct. 10, 2008), pp. 359-367.

Cho et al. System biology of interstitial lung diseases: integration of mRNA and microRNA expression changes. 2011, BMC Medical Genomics, 4:8, p. 1-20.

Thisteda. What is a P-value. Departments of Statistics and Health Studies. The University of Chicago. (May 25, 1988).

Spira, Avrum E. Abstract: Airway gene expression in smokers: an early diagnostic biomarker for lung cancer. National Institutes of Health Grant No. 1 RO1 CA124640-01 (Funding Start Date May 1, 2007).

Spira, Avrum E. Abstract: The airway transcriptome as a biomarker for lung cancer. National Institutes of Health Grant No. 1 R21 CA106506-01A2 (Funding Start Date Aug. 9, 2005).

Spira, et al. Airway epithelial gene expression in the diagnostic evaluation of smokers with suspect lung cancer. Nature Medicine 13: 361-366 (2007).

Spira, et al. Effects of cigarette smoke on the human airway epithelial cell transcriptome. PNAS, 101: 27, p. 10143-10148 (Jul. 6, 2004).

Spira et al. Gene Expression Profiling of Human Lung Tissue from Smokers with Severe Emphysema. Am J Respir Cell Mol Biol. Dec. 2004;31(6):601-10.

Spira, et al. Impact of cigarette smoke on the normal airway transcriptome. Chest. 125 (5 Suppl):115S (May 2004).

Spira et al. Noninvasive method for obtaining RNA from buccal mucosa epithelial cells for gene expression profiling. Biotechniques, 36(3): 484-7 (Apr. 2004).

Spivack, et al. Gene-environment interaction signatures by quantitative mRNA profiling in exfoliated buccal mucosal cells. Cancer Res. Sep. 15, 2004;64(18):6805-13.

Sridhar et al. Smoking-induced gene expression changes in the bronchial airway are reflected in nasal and buccal epithelium. BMC Genomics, 9: 259 (May 2008).

St. Croix et al. Genes Expressed in Human Tumor Endothelium. Science, 289:1197-1202, (Aug. 18, 2000).

Steiling et al: "A Dynamic Bronchial Airway Gene ExpressionSignature of Chronic Obstructive Pulmonary Disease and Lung Function Impairment",American Journal of Respiratory and Critical Care Medicine, val. 187, No. 9, (Mar. 7, 2013), pp. 933-942.

Steiling et al. The field of tissue injury in the lung and airway. Cancer Prevention Research (2008); 1.6: 396-403.

Stephenson et al. Integration of gene expression profiling and clinical variables to predict prostate carcinoma recurrence after radical prostatectomy. Cancer 2005; 104:290-8, 2005.

Stewart, JH. Lung Carcinoma in African Americans, A Review of the Current Literature. Cancer; 91(12): 2476-2482 (Jun. 15, 2001).

Strausberg et al. Reading the Molecular Signatures of Cancer. Microarrays and Cancer Research, Warrington et al. (eds.), Eaton Publishing, Westborough, MA, pp. 81-111, (2002).

Su et al. Molecular Classification of Human Carcinomas by Use of Gene Expression Signatures. Cancer Research, 61:7388-7393, (Oct. 15, 2001).

Subramanian et al. Gene set enrichment analysis: a knowledge-based approach for interpreting genome-wide expression profiles. PNAS USA 102:15545-15550 (2005).

Sugita et al. Combined Use of Oligonucleotide and Tissue Microarrays Identifies Cancer/Testis Antigens as Biomarkers in Lung Carcinoma. Cancer Research. Jul. 2002. vol. 62, Issue 14, pp. 3971-3979.

Sumikawa et al. Computed tomography findings in pathological usual interstitial pneumonia: relationship to survival. American Journal of Respiratory and Critical Care Medicine (2008); 177.4: 433-439.

Suomalainen et al. Quantitative analysis of human DNA sequences by PCR and solid-phase minisequencing. Molecular Biotechnology (2000); 15.2: 123-131.

Suykens et al. Least squares support vector machine classifiers. Neural Processing Letters (1999); 9.3: 293-300.

Suzanne A Eccles et al: "Metastasis: recent discoveries and novel treatment strategies", The Lancet, val. 369, No. 9574, May 1, 2007 (May 1, 2007 ), pp. 1742-1757, XP055231616.

Swensen et al. Solitary pulmonary nodules: clinical prediction model versus physicians. Mayo Clinic Proc 1999; 74:319-29 (1999).

Swensen et al. The probability of malignancy in solitary pulmonary nodules. Application to small radiologically indeterminate nodules. Arch Intern Med 1997; 157:849-55, 1997.

Takizawa et al. Increased expression of transforming growth factor-betal in small airway epithelium from tobacco smokers and patients with chronic obstructive pulmonary disease (COPD). American Journal of Respiratory and Critical Care Medicine, 163:1476-1483 (2001).

Tanaka et al. Trial to establish an animal model of paraneoplastic cerebellar degeneration with anti-Yo antibody: 1. Mouse strains bearing different MHC molecules produce antibodies on immunization with recombinant Yo protein, but do not cause Purkinje cell loss. Clinical Neurology and Neurosurgery (1995); 97.1: 95-100.

Tanoue et al. Lung cancer screening. American Journal of Respiratory and Critical Care Medicine (2015); 191.1: 19-33.

Tarca et al. Analysis of microarray experiments of gene expression profiling. Am J Obstet Gynecol 195(2): 373-388 (Aug. 2006).

Team, R. Core. R: A language and environment for statistical computing. R Foundation for Statistical Computing, Vienna, Austria (2013): pp. 1-14.

Theocharis et al. Metallothionein: a multifunctional protein from toxicity to cancer. Int Biol Markers, 18(3):162-169 (2003).

Thurston et al. Modeling lung cancer risk in case-control studies using a new dose metric of smoking. Cancer Epidemiol Biomarkers Prey 2005; 14(10): 2296-302 (2005).

Tibshirani. Regression shrinkage and selection via the lasso. Journal of the Royal Statistical Society Series B (Methodological) 58:267-288 (1996).

Tichelaar et al. Increased staining for phospho-Akt, p65/RELA and clAP-2 in pre-neoplastic human bronchial biopsies. BMC Cancer 5(155):1-13 (2005).

Tomassetti et al. Bronchoscopic lung cryobiopsy increases diagnostic confidence in the multidisciplinary diagnosis of idiopathic pulmonary fibrosis. American Journal of Respiratory and Critical Care Medicine (2016); 193.7: 745-752.

Tomassetti et al. Transbronchial biopsy is useful in predicting UIP pattern. Respiratory Research (2012); 13.1: 96.

Trahan et al. Role of surgical lung biopsy in separating chronic hypersensitivity pneumonia from usual interstitial pneumonia/idiopathic pulmonary fibrosis: analysis of 31 biopsies from 15 patients. CHEST Journal (2008); 134.1: 126-132.

Trapnell, et al. TopHat: discovering splice junctions with RNA-Seq. Bioinformatics. May 1, 2009;25(9):1105-11. doi: 10.1093/bioinformatics/btp120. Epub Mar. 16, 2009.

Travis et al. An official American Thoracic Society/European Respiratory Society statement: Update of the international multidisciplinary classification of the idiopathic interstitial pneumonias. Am J Respir Crit Care Med (2013); 188.6: 733-748.

Treutlein et al. Reconstructing lineage hierarchies of the distal lung epithelium using single-cell RNA-seq. Nature. May 15, 2014;509(7500):371-5. doi: 10.1038/nature13173. Epub Apr. 13, 2014.

Trunk et al. The management and evaluation of the solitary pulmonary nodule. Chest 1974; 66:236-9 (1974).

Tsao et al. Increased Phospho-AKT (Ser4(3) Expression in Bronchial Dysplasia: Implications for Lunch Cancer Prevention Studies. Cancer Epidemiology Biomarkers & Prevention. 12:660-664 (2003).

(56) References Cited

OTHER PUBLICATIONS

Tsukamoto et al. Involvement of gicerin, a cell adhesion molecule, in tracheal development and regeneration. Cell Growth and Differentiation-Publication Cell Growth & Differentiation (1996); 7.12: 1761-1768.

Tsukamoto et al. The role of gicerin, a novel cell adhesion molecule, in development, regeneration and neoplasia. Histology and Histopathology (2001); 16.2: 563-571.

Tukey et al. Population-based estimates of transbronchial lung biopsy utilization and complications. Respiratory Medicine (2012); 106.11: 1559-1565.

Ung et al. 18Fluorodeoxyglucose positron emission tomography in the diagnosis and staging of lung cancer: a systematic review. J Nat'l Cancer Institute, 99(23): 1753-67 (2007).

Volm et al. Prognostic significance of the expression of c-fos, c-jun and c-erbB-1 oncogene products in human squamous cell lung carcinomas. J Cancer Res Clin Oncol, 119: 507-510 (1993).

Voynow et al. UC2, and MUC5/5AC in Nasal Epithelial Cells of Cystic Fibrosis, Allergic Rhinitis, and Normal Individuals. Lung 176: 345-354 (1998).

Wahidi, et al. Evidence for the treatment of patients with pulmonary nodules: when is it lung cancer? ACCP evidence-based clinical practice guidelines 2nd Edition. Chest 2007; 132:94-1075 (2007).

Wardlaw et al. Effect of cigarette smoke on CYP1A1, CYP1A2 and CYP2B1/2 of nasal mucosae in F344 rats. Carcinogenesis 19(4): 655-662 (1998).

Watters et al. Developing Gene Expression Signatures of Pathway Deregulation in Tumors. Molecular Cancer Therapeutics, 5: 2444-2449, Oct. 2006.

Wells, Athol U. Managing diagnostic procedures in idiopathic pulmonary fibrosis. European Respiratory Review (2013); 22.128: 158-162.

Wells, Athol U. The revised ATS/ERS/JRS/ALAT diagnostic criteria for idiopathic pulmonary fibrosis (IPF)-practical implications. Respiratory Research (2013); 14(Suppl 1):S2.

West et al. Embracing the complexity of genomic data for personalized medicine. Genome Res 2006; 16:559-66, May 2006.

West et al. Rapid Akt Activation by Nicotine and Tobacco Carcinogen Modulates the Phenotype of Normal Human Airway Epithelial Cells. The Journal of Clinical Investigation. 111(1):81-90 (Jan. 2003).

Whitehead, et al. Variation in tissue-specific gene expression among natural populations. Genome Biol. 2005;6(2):R13. Epub Jan. 26, 2005.

Whitney et al. Derivation of a bronchial genomic classifier for lung cancer in a prospective study of patients undergoing diagnostic bronchoscopy. BMC Med Genomics. May 6, 2015;8:18.

Wiener et al. An official American Thoracic Society/American College of Chest Physicians policy statement: implementation of low-dose computed tomography lung cancer screening programs in clinical practice. Am J Respir Crit Care Med. Oct. 1, 2015;192(7):881-91.

Wiener et al. Population-based risk for complications after transthoracic needle lung biopsy of a pulmonary nodule: an analysis of discharge records. Annals of Internal Medicine (2011); 155.3: 137-144.

Wiener et al. Risks of transthoracic needle biopsy: how high? Clinical Pulmonary Medicine (2013); 20.1: 29.

Wilkerson et al. ConsensusClusterPlus: a class discovery tool with confidence assessments and item tracking. Bioinformatics (2010); 26.12: 1572-1573.

Willey et al. Quantitative RT-PCR Measurement of Cytochromes p450 1A1, 1b1, and 2B7, Microsomal Epoxide Hydrolase, and NADPH Oxidoreductase Expression in Lung Cells of Smokers and Nonsmokers. Am. J. Respir. Cell Mol. Biol., 1997, 17:114-124.

Wistuba et al. High resolution chromosome 3p allelotyping of human lung cancer and preneoplastic/preinvasive bronchial epithelium reveals multiple, discontinuous sites of 3p allele loss and three regions of frequent breakpoints. Cancer Res., 60(7): 1949-60 (Apr. 1, 2000).

Wistuba et al. Molecular damage in the bronchial epithelium of current and former smokers. J Natl Cancer Inst., 89(18): 1366-73 (Sep. 17, 1997).

Woenckhaus et al. Expression Profiling of Non-Small Cell Lung Cancers and Bronchi of Smokers and Non Smokers. Study Group: Molecular Pathology/Pathology—Research and Practice, 200:p. 255, (2004).

Woenckhaus et al. Smoking and cancer-related gene expression in bronchial epithelium and non-small-cell lung cancers. Journal of Pathology, 210: 192-204 (Oct. 2006).

Wojnarowski et al. Cytokine Expression in Bronchial Biopsies of Cystic Fibrosis Patients With and Without Acute Exacerbation. (Eur Respir, 1999, 14: 1136-114).

Woodcock et al. The treatment of idiopathic pulmonary fibrosis. F1000Prime Rep. Mar. 3, 2014;6:16.

Wu, Thomas D. Analysing gene expression data from DNA microarrays to identify candidate genes. Journal of Pathology, 195:53-65 (2001).

Wuenschell et al. Embryonic mouse lung epithelial progenitor cells co-express immunohistochemical markers of diverse mature cell lineages. Journal of Histochemistry and Cytochemistry (1996); 44.2: 113-123.

Yang et al. Expression of cilium-associated genes defines novel molecular subtypes of idiopathic pulmonary fibrosis. Thorax (2013): 68(12):1114-11121.

Yang et al. Gene expression profiling of familial and sporadic interstitial pneumonia. American Journal of Respiratory and Critical Care Medicine (2007); 175.1: 45-54.

Yang et al. Reduction of Dihydrodiol Dehydrogenase Expression in Resected Hepatocellular Carcinoma. OncoL Rep., 10(2):271-276, (2003).

Yen-Tsung Huang et al., "Genome-Wide Analysis of Survival in Early-Stage Non-Small-Cell Lung Cancer", Journal of Clinical Oncology, Jun. 1, 2009, 27 (16), 2660-2667.

Yoneda et al. Development of High-Density DNA Microarray Membrane for Profiling Smoke- and Hydrogen Peroxide-Induced Genes in a Human Bronchial Epithelial Cell Line. American Journal of Respiratory and Critical Care Medicine, 164:S86-S89, (2001).

Yu-Rong, et al. Tumor-associated antisen L6 and the invasion of human lung cancer cells. Clinical Cancer Research, Jul. 2003; vol. 9: 2807-2816.

Zeeberg et al. GoMiner: a resource for biological interpretation of genomic and proteomic data. Genome Biology, 4(4):R28.1-R28.8 (Mar. 2003).

Zemke et al. Molecular staging of epithelial maturation using secretory cell-specific genes as markers. American Journal of Respiratory Cell and Molecular Biology (2009); 40.3: 340-348.

Zeskind Julie E et al: "Translating the COPD transcriptome: insights into pathogenesis and tools for clinical anagement.",Proceedings of the American Thoracic Society Dec. 1, 2008, vol. 5, No. 8, Dec. 1, 2008 (Dec. 1, 2008), pp. 834-841.

Zhang et al. Comparison of smoking-induced gene expression on Affymetrix Exon and 3'-based expression arrays. Genome Inform. 18: 247-57 (2007).

Zhang et al. Similarities and differences between smoking-related gene expression in nasal and bronchial epithelium. Physiological Genomics (2010); 41(1), 1-8.

Zochbauer-Muller et al. 5' CpG Island Methylation of the FHIT Gene is Correlated with Loss of Gene Expression in Lung and Breast. Cancer Research, 61:3581-3585, (May 2, 2001).

\* cited by examiner

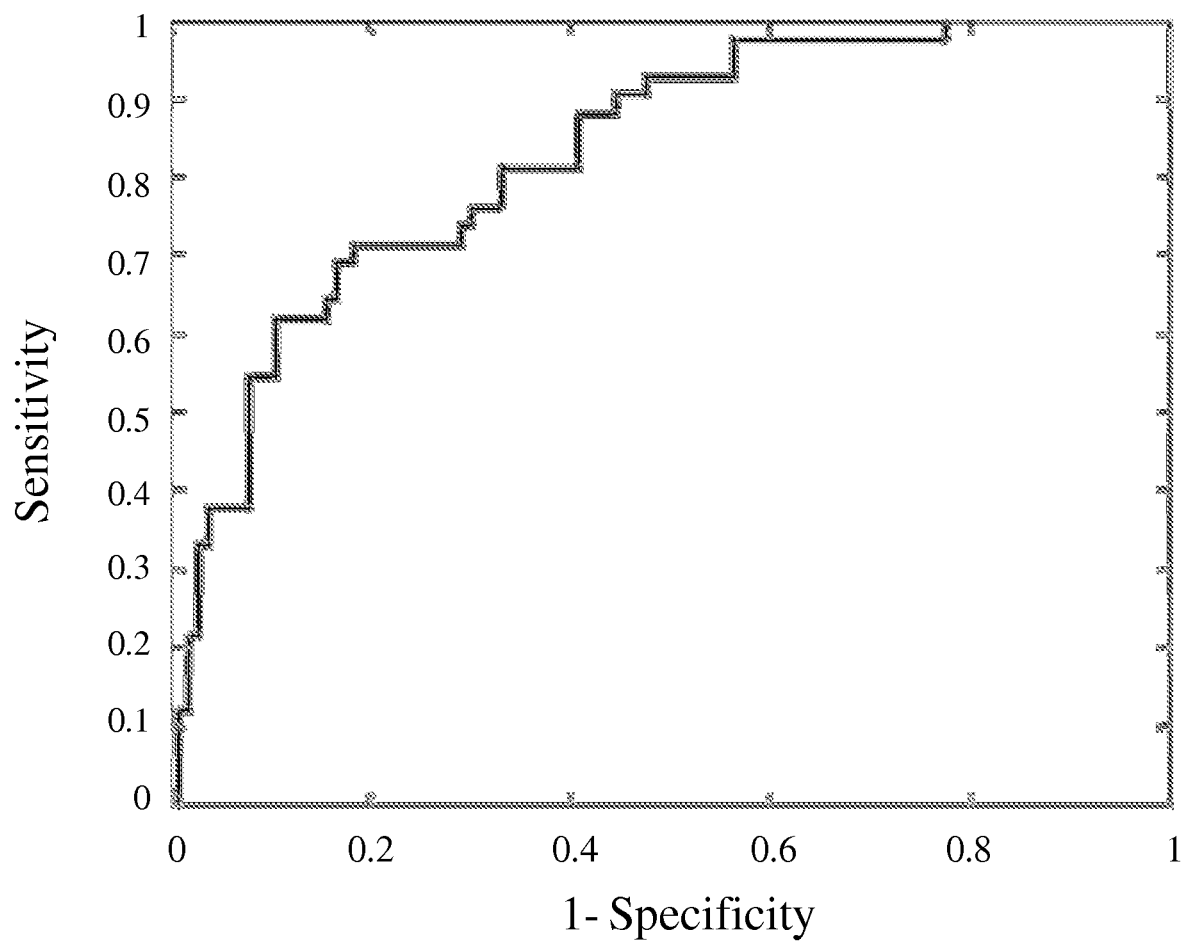

METHODS FOR EVALUATING COPD STATUS

CROSS-REFERENCE TO RELATED APPLICATION

This application is a U.S. national phase of International Application No. PCT/US2014/025715, filed Mar. 13, 2014, which claims the benefit under 35 U.S.C. § 119(e) of the filing date of U.S. Provisional Application No. 61/783,983, filed Mar. 14, 2013. The entire contents of these referenced applications are incorporated by reference herein.

FIELD OF THE INVENTION

The invention generally relates to methods and compositions for assessing pulmonary disease risk using genomic information.

BACKGROUND OF INVENTION

Chronic obstructive pulmonary disease (COPD) is a group of lung conditions, including emphysema, chronic bronchitis, and bronchiectasis, which are characterized by largely irreversible airflow obstruction. COPD causes considerable morbidity and mortality. Currently, it represents the fourth leading cause of death in the world, and it is expected to increase both in prevalence and in mortality over the next decades.

SUMMARY OF INVENTION

Provided herein are methods for characterizing the COPD status of a subject. In some embodiments, methods provided herein are useful for establishing appropriate diagnostic intervention plans and/or treatment plans for subjects having or suspected of having COPD, and for aiding healthcare providers in establishing such plans. Accordingly, in some embodiments, methods provided herein are useful for diagnosing COPD in subjects and managing treatment of such subjects. In some embodiments, methods are provided that involve assessing the COPD status of a subject based on expression levels of informative-genes in a biological sample obtained from a subject during a routine cell or tissue sampling procedure. In some embodiments, methods are provided that involve establishing COPD risk scores based on expression levels of informative-genes. In some embodiments, appropriate diagnostic intervention plans are established based at least in part on the COPD risk scores. In some embodiments, the methods assist health care providers with making early and accurate diagnoses. In some embodiments, the methods assist health care providers with establishing appropriate therapeutic interventions early on in patient clinical evaluations. In some embodiments, the methods involve evaluating biological samples obtained during bronchoscopic procedures. In some embodiments, the methods are beneficial because they enable health care providers to make informative decisions regarding patient diagnosis and/or treatment from otherwise uninformative bronchoscopies. In some embodiments, the risk assessment leads to appropriate surveillance for monitoring low risk lesions. In some embodiments, the risk assessment leads to faster diagnosis, and thus, faster treatment for COPD.

Certain methods described herein, alone or in combination with other methods, provide useful information for health care providers to assist them in making diagnostic and treatment decisions for a patient. Certain methods disclosed herein are employed in instances where other methods have failed to provide useful information regarding the COPD status of a patient. Certain methods disclosed herein provide an alternative or complementary method for evaluating cell or tissue samples obtained during routine bronchoscopy procedures, and increase the likelihood that the procedures will result in useful information for managing a patient's care. The methods disclosed herein are highly sensitive, and produce information regarding the likelihood that a subject has COPD from cell or tissue samples (e.g., histologically normal tissue) that may be obtained from positions remote from diseased tissue. Certain methods described herein can be used to assess the likelihood that a subject has COPD by evaluating histologically normal cells or tissues obtained during a routine cell or tissue sampling procedure (e.g., standard ancillary bronchoscopic procedures such as brushing, biopsy, lavage, and needle-aspiration). However, it should be appreciated that any suitable tissue or cell sample can be used. Often the cells or tissues that are assessed by the methods appear histologically normal.

In some embodiments, the methods are useful for confirming that a subject has or does not have COPD. According to some aspects of the invention, methods are provided for evaluating the COPD status of a subject using gene expression information that involve one or more of the following acts: (a) obtaining a biological sample from the respiratory tract of a subject, (b) subjecting the biological sample to a gene expression analysis, in which the gene expression analysis comprises determining the expression levels of a plurality of informative-genes in the biological sample, (c) computing a COPD risk score based on the expression levels of the plurality of informative-genes, (d) determining that the subject is in need of a first diagnostic intervention to evaluate COPD status, if the level of the COPD risk score is beyond (e.g., above) a first threshold level, and (e) determining that the subject is in need of a second diagnostic intervention to evaluate COPD status, if the level of the COPD risk score is beyond (e.g., below) a second threshold level. In some embodiments, the subject has been identified as a candidate for bronchoscopy and/or as having a suspicious lesion in the respiratory tract. In some embodiments, the subject is not a candidate for bronchoscopy. For example, a subject may have such severe airway damage that bronchoscopy is not possible. In some embodiments, the methods further comprise (f) determining that the subject is in need of a third diagnostic intervention to evaluate COPD status, if the level of the COPD risk score is between the first threshold and the second threshold levels.

In some embodiments, a diagnostic intervention (e.g., first or second or third intervention) comprises performing spirometry on the subject to evaluate pulmonary function. In some embodiments, spirometry is used to determine a forced expiratory volume in one second. Forced Expiratory Volume in one second ($FEV_1$) is the amount of air which can be forcibly exhaled from the lungs of a subject in the first second of a forced exhalation. In some embodiments, spirometry is used to determine a forced vital capacity. Forced vital capacity (FVC) is the volume of air that can forcibly be blown out by a subject after full inspiration. In some embodiments, a diagnostic intervention (e.g., first or second or third intervention) comprises assessing whether a subject has irreversible airflow obstruction. In some embodiments, irreversible airflow obstruction is assessed by determining a post-bronchodilator forced expiratory volume in one second to forced vital capacity ratio ($FEV_1/FVC$). In some embodiments, a $FEV_1/FVC$ of less than 0.7 or less than 0.75 is indicative of irreversible airflow obstruction.

In some embodiments, a diagnostic intervention (e.g., first or second or third intervention) comprises engaging in watchful waiting (or monitoring). In some embodiments, watchful waiting comprises periodically performing spirometry to evaluate lung function or imaging the respiratory tract to evaluate tissue. In some embodiments, watchful waiting comprises periodically performing spirometry to evaluate lung function or imaging the respiratory tract to evaluate a tissue for up to one year, two years, four years, five years or more. In some embodiments, watchful waiting comprises performing spirometry to evaluate lung function or imaging the respiratory tract to evaluate tissue at least once per year. In some embodiments, watchful waiting comprises performing spirometry to evaluate lung function or imaging the respiratory tract to evaluate tissue at least twice per year.

In some embodiments, watchful waiting (or monitoring) comprises periodically repeating steps (a) to (e). In some embodiments, watchful waiting comprises periodically repeating steps (a) to (f). In some embodiments, the third diagnostic intervention comprises performing a bronchoscopy or spirometry or other procedure to evaluate lung function or health. In some embodiments, the third diagnostic intervention comprises repeating steps (a) to (e). In certain embodiments, the third diagnostic intervention comprises repeating steps (a) to (e) within six months of determining that the COPD risk score is between the first threshold and the second threshold levels. In certain embodiments, the third diagnostic intervention comprises repeating steps (a) to (e) within three months of determining that the COPD risk score is between the first threshold and the second threshold levels. In some embodiments, the third diagnostic intervention comprises repeating steps (a) to (e) within one month of determining that the COPD risk score is between the first threshold and the second threshold levels.

Any one or more of a number of different treatment interventions may be established for a subject identified as having COPD or at risk of having COPD according to methods provided herein. In some embodiments, the intervention is aiding the subject in a smoking cessation program, which may or may not involve treatment with a therapeutic to minimize withdrawal side-effects or a nicotine replacement agent. In some embodiment, pharmacologic and/or non-pharmacologic therapy for COPD is used to reduce symptoms, reduce the frequency and severity of exacerbations, and/or improve health status and exercise tolerance. In some embodiment, a therapy for COPD is selected based on the results of the assessment or diagnostic methods disclosed herein. In some embodiments, a pharmacologic therapy for COPD is selected from: beta2-agonists that are short-acting, such as fenoterol, levalbuterol, salbutamol (albuterol), and terbutaline; beta2-agonists that are long-acting, such as formoterol, arformoterol, indacaterol, salmeterol and tulobuterol; anticholinergics that are short-acting, such as ipratropium bromide and oxitropium bromide; anticholinergics that are long-acting, such as aclidinium bromide, glycopyrronium bromide and tiotropium; a combination short-acting beta2-agonists plus anticholinergic in one inhaler, such as fenoterol/ipratropium and salbutamol/ipratropium; methylxanthines such as aminophylline and theophylline; inhaled corticosteroids such as beclomethasone, budesonide and fluticasone; a combination long-acting beta2-agonists plus corticosteroids in one inhaler, such as formoterol/budesonide, formoterol/mometasone and salmeterol/fluticasone; systemic corticosteroids such as prednisone and methyl-prednisolone; and phosphodiesterase-4 inhibitors such as roflumilast. In some embodiments, a non-pharmacologic therapy for COPD is selected from: pulmonary rehabilitation (e.g., to reduce symptoms, improve quality of life, and/or increase physical and emotional participation in everyday activities); oxygen therapy (e.g., long-term administration of oxygen (>15 hours per day) to patients with chronic respiratory failure); ventilatory support; surgical treatment, such as lung volume reduction surgery (LVRS); bronchoscopic lung volume reduction (BLVR), lung transplantation, or bullectomy; a smoking cessation program; and physical activity.

In some embodiments, the plurality of informative genes comprises informative-mRNAs. In some embodiments, the plurality of informative genes comprises at least two informative-mRNAs. In some embodiments, the plurality of informative genes is selected from the group of genes in Table 2. In some embodiments, the expression levels of a subset of these genes are evaluated and compared to reference expression levels (e.g., for normal patients that do not have COPD). In some embodiments, the subset includes a) genes for which an increase in expression is associated with COPD or an increased risk for COPD, b) genes for which a decrease in expression is associated with COPD or an increased risk for COPD, or both. In some embodiments, at least 5%, at least 10%, at least 20%, at least 30%, at least 40%, or about 50% of the genes in a subset have an increased level of expression in association with an increased risk for COPD. In some embodiments, at least 5%, at least 10%, at least 20%, at least 30%, at least 40%, or about 50% of the genes in a subset have a decreased level of expression in association with an increased risk for COPD. In some embodiments, an expression level is evaluated (e.g., assayed or otherwise interrogated) for each of 10-80 or more genes (e.g., 5-10, 10-20, 20-30, 30-40, 40-50, 50-60, 60-70, 70-80, about 10, about 15, about 25, about 35, about 45, about 55, about 65, about 75, or more genes) selected from the genes in Table 2. In some embodiments, expression levels for one or more control genes also are evaluated (e.g., 1, 2, 3, 4, or 5 of the control genes). It should be appreciated that an assay can also include other genes, for example reference genes or other gene (regardless of how informative they are). However, if the expression profile for any of the informative gene subsets described herein is indicative of an increased risk for COPD, then an appropriate therapeutic or diagnostic recommendation can be made as described herein.

In some embodiments, the identification of changes in expression level of one or more subsets of genes from Table 2 can be provided to a physician or other health care professional in any suitable format. These gene expression profiles alone may be sufficient for making a diagnosis, providing a prognosis, or for recommending further diagnosis or a particular treatment. However, in some embodiments the gene expression profiles may assist in the diagnosis, prognosis, and/or treatment of a subject along with other information (e.g., other mRNA or miRNA expression information, and/or other physical or chemical information about the subject, including family history).

In some embodiments, a subject is identified as having a suspicious lesion in the respiratory tract by imaging the respiratory tract. In certain embodiments, imaging the respiratory tract comprises performing computer-aided tomography, magnetic resonance imaging, ultrasonography or a chest X-ray.

Methods are provided, in some embodiments, for obtaining biological samples from patients. Expression levels of informative-genes in these biological samples provide a basis for assessing the likelihood that the patient has COPD.

Methods are provided for processing biological samples. In some embodiments, the processing methods ensure RNA quality and integrity to enable downstream analysis of informative-genes and ensure quality in the results obtained. Accordingly, various quality control steps (e.g., RNA size analyses) may be employed in these methods. Methods are provided for packaging and storing biological samples. Methods are provided for shipping or transporting biological samples, e.g., to an assay laboratory where the biological sample may be processed and/or where a gene expression analysis may be performed. Methods are provided for performing gene expression analyses on biological samples to determine the expression levels of informative-genes in the samples. Methods are provided for analyzing and interpreting the results of gene expression analyses of informative-genes. Methods are provided for generating reports that summarize the results of gene expression analyses, and for transmitting or sending assay results and/or assay interpretations to a health care provider (e.g., a physician). Furthermore, methods are provided for making treatment decisions based on the gene expression assay results, including making recommendations for further treatment or invasive diagnostic procedures.

In some embodiments, aspects of the invention are based, at least in part, on the determination that the expression level of certain informative-genes in apparently histologically normal cells obtained from a first airway locus can be used to evaluate the likelihood of COPD at a second locus in the airway (for example, at a locus in the airway that is remote from the locus at which the histologically normal cells were sampled).

In some embodiments, aspects of the invention relate to determining the likelihood that a subject has COPD, by subjecting a biological sample obtained from a subject to a gene expression analysis, wherein the gene expression analysis comprises determining expression levels in the biological sample of at least one informative-genes (e.g., at least two mRNAs selected from Table 2), and using the expression levels to assist in determining the likelihood that the subject has COPD.

In some embodiments, the step of determining comprises transforming the expression levels into a COPD risk-score that is indicative of the likelihood that the subject has COPD. In some embodiments, the COPD risk-score is the combination of weighted expression levels. In some embodiments, the COPD risk-score is the sum of weighted expression levels. In some embodiments, the expression levels are weighted by their relative contribution to predicting increased likelihood of having COPD.

In some embodiments, aspects of the invention relate to determining a treatment course for a subject, by subjecting a biological sample obtained from the subject to a gene expression analysis, wherein the gene expression analysis comprises determining the expression levels in the biological sample of at least two informative-genes (e.g., at least two mRNAs selected from Table 2), and determining a treatment course for the subject based on the expression levels. In some embodiments, the treatment course is determined based on a COPD risk-score derived from the expression levels. In some embodiments, the subject is identified as a candidate for a COPD therapy based on a COPD risk-score that indicates the subject has a relatively high likelihood of having COPD. In some embodiments, the subject is identified as a candidate for an invasive lung procedure based on a COPD risk-score that indicates the subject has a relatively high likelihood of having COPD. In some embodiments, the invasive lung procedure is a transthoracic needle aspiration, mediastinoscopy or thoracotomy. In some embodiments, the subject is identified as not being a candidate for a COPD therapy or an invasive lung procedure based on a COPD risk-score that indicates the subject has a relatively low likelihood of having COPD. In some embodiments, a report summarizing the results of the gene expression analysis is created. In some embodiments, the report indicates the COPD risk-score.

In some embodiments, aspects of the invention relate to determining the likelihood that a subject has COPD by subjecting a biological sample obtained from a subject to a gene expression analysis, wherein the gene expression analysis comprises determining the expression levels in the biological sample of at least one informative-gene (e.g., at least one informative-mRNA selected from Table 2), and determining the likelihood that the subject has COPD based at least in part on the expression levels.

In some embodiments, aspects of the invention relate to determining the likelihood that a subject has COPD, by subjecting a biological sample obtained from the respiratory epithelium of a subject to a gene expression analysis, wherein the gene expression analysis comprises determining the expression level in the biological sample of at least one informative-gene (e.g., at least one informative-mRNA selected from Table 2), and determining the likelihood that the subject has COPD based at least in part on the expression level, wherein the biological sample comprises histologically normal tissue.

In some embodiments, aspects of the invention relate to a computer-implemented method for processing genomic information, by obtaining data representing expression levels in a biological sample of at least two informative-genes (e.g., at least two informative-mRNAs from Table 2), wherein the biological sample was obtained of a subject, and using the expression levels to assist in determining the likelihood that the subject has COPD. A computer-implemented method can include inputting data via a user interface, computing (e.g., calculating, comparing, or otherwise analyzing) using a processor, and/or outputting results via a display or other user interface.

In some embodiments, the step of determining comprises calculating a risk-score indicative of the likelihood that the subject has COPD. In some embodiments, computing the risk-score involves determining the combination of weighted expression levels, wherein the expression levels are weighted by their relative contribution to predicting increased likelihood of having COPD. In some embodiments, a computer-implemented method comprises generating a report that indicates the risk-score. In some embodiments, the report is transmitted to a health care provider of the subject.

It should be appreciated that in any embodiment or aspect described herein, a biological sample can be obtained from the respiratory epithelium of the subject. The respiratory epithelium can be of the mouth, nose, pharynx, trachea, bronchi, bronchioles, or alveoli. However, other sources of respiratory epithelium also can be used. The biological sample can comprise histologically normal tissue. The biological sample can be obtained using bronchial brushings, broncho-alveolar lavage, or a bronchial biopsy. The subject can exhibit one or more symptoms of COPD and/or have a lesion that is observable by computer-aided tomography or chest X-ray.

In any of the embodiments or aspects described herein, the expression levels can be determined using a quantitative reverse transcription polymerase chain reaction, a bead-based nucleic acid detection assay, an oligonucleotide array assay, or other technique.

In some embodiments, aspects of the invention relate to a composition consisting essentially of at least one nucleic acid probe, wherein each of the at least one nucleic acids probe specifically hybridizes with an informative-gene (e.g., at least one informative-mRNA selected from Table 2).

In some embodiments, aspects of the invention relate to a composition comprising up to 5, up to 10, up to 25, up to 50, up to 100, or up to 200 nucleic acid probes, wherein each of at least two of the nucleic acid probes specifically hybridizes with an informative-gene (e.g., at least one informative-mRNA selected from Table 2).

In some embodiments, nucleic acid probes are conjugated directly or indirectly to a bead. In some embodiments, the bead is a magnetic bead. In some embodiments, the nucleic acid probes are immobilized to a solid support. In some embodiments, the solid support is a glass, plastic or silicon chip.

In some embodiments, aspects of the invention relate to a kit comprising at least one container or package housing any nucleic acid probe composition described herein.

In some embodiments, expression levels are determined using a quantitative reverse transcription polymerase chain reaction.

According to some aspects of the invention, kits are provided that comprise primers for amplifying at least one informative-genes selected from Table 2. In some embodiments, the kits (e.g., gene arrays) comprise at least one primer for amplifying at least 1, at least 2, at least 3, at least 4, at least 5, at least 6, at least 7, at least 8, at least 9, at least 10, or at least 20 informative-genes selected from Table 2. In some embodiments, the kits (e.g., gene arrays) comprise at least one primer for amplifying up to 5, up to 10, up to 25, up to 50, up to 75, up to 100 informative-genes selected from Table 2. In some embodiments, the kits comprise primers that consist essentially of primers for amplifying each of the informative-genes listed in Table 2. In some embodiments, the gene arrays comprise primers for amplifying one or more control genes, such as ACTB, GAPDH, YWHAZ, POLR2A, DDX3Y, or other control genes. In some embodiments, ACTB, GAPDH, YWHAZ, and POLR2A are used as control genes for normalizing expression levels. In some embodiments, DDX3Y is a semi-identity control because it is a gender specific gene, which is generally more highly expressed in males than females. Thus, DDX3Y can be used in some embodiments to determine whether a sample is from a male or female subject. This information can be used to confirm accuracy of personal information about a subject and exclude samples during data analysis if the information is inconsistent with DDX3Y expression information. For example, if personal information indicates that a subject is female but DDX3Y is highly expressed in a sample (indicating a male subject), the sample can be excluded.

Control genes can be used for normalization singularly or in any combination including with one or more additional control genes.

These and other aspects are described in more detail herein and are illustrated by the non-limiting figures and examples.

BRIEF DESCRIPTION OF THE DRAWINGS

FIG. 1 is a ROC curve for a COPD gene-signature that differentiates subjects with and without COPD, resulting in an overall AUC of >0.80.

DETAILED DESCRIPTION OF CERTAIN EMBODIMENTS OF THE INVENTION

In some embodiments, aspects of the invention relate to genes for which expression levels can be used to determine the likelihood that a subject (e.g., a human subject) has COPD. As used herein, "chronic obstructive pulmonary disease", or "COPD," is a disease characterized by a persistent airflow limitation that is usually progressive and associated with an enhanced chronic inflammatory response in the airways and the lung to noxious particles or gases. In some embodiments, the chronic airflow limitation characteristic of COPD is caused by small airway disease (obstructive bronchiolitis) and/or parenchymal destruction (emphysema). In some embodiments, chronic inflammation causes structural changes and narrowing of the small airways and narrowing of the small airways. In some embodiments, destruction of the lung parenchyma, which also may be due to inflammatory processes, leads to the loss of alveolar attachments to the small airways and decreased lung elastic recoil. In some embodiments, these changes diminish the ability of the airways to remain open during expiration. In some embodiments, airflow limitation associated with COPD may be measured by spirometry, which is a widely available, reproducible test of lung function. In some embodiments, COPD is a disease classified by World Health Organization (WHO), according to the International Statistical Classification of Diseases and Related Health Problems 10th Revision (ICD-10), within the category of "COPD and allied conditions" (ICD-10 codes J42-46).

In some embodiments, methods provided herein comprise monitoring COPD progression and development of complications associated with COPD. In some of such embodiments, the methods may include, for example, monitoring expression of one or more of the informative-genes of Table 2; evaluating lung function by spirometry (e.g., at least once a year); evaluating smoking status and environment exposures (e.g., at least once per year); monitoring pharmacotherapy and other medical treatments for COPD; monitoring exacerbation history; and/or monitoring the presence or absence of comorbidities.

In some embodiments, COPD is diagnosed, at least in part, by using a pulmonary function test. In some embodiments, COPD is coincident with emphysema. In some embodiments, a subject who has COPD has increased risk of developing lung cancer. In some embodiments, COPD it is indicative of a premalignant state.

In some embodiments, the expression levels (e.g., mRNA levels) of one or more genes described herein can be determined in airway samples (e.g., epithelial cells or other samples obtained during a bronchoscopy or from an appropriate bronchial lavage samples). In some embodiments, the patterns of increased and/or decreased mRNA expression levels for one or more subsets of useful genes (e.g., 1-5, 5-10, 10-15, 15-20, 20-25, 25-50, 50-80, or more genes) described herein can be determined and used for diagnostic, prognostic, and/or therapeutic purposes. It should be appreciated that one or more expression patterns described herein can be used alone, or can be helpful along with one or more additional patient-specific indicia or symptoms, to provide personalized diagnostic, prognostic, and/or therapeutic predictions or recommendations for a patient.

In some embodiments, provided herein are methods for establishing appropriate diagnostic intervention plans and/or treatment plans for subjects and for aiding healthcare providers in establishing appropriate diagnostic intervention plans and/or treatment plans. In some embodiments, methods are provided that involve making a risk assessment based on expression levels of informative-genes in a biological sample obtained from a subject during a routine cell or tissue sampling procedure. In some embodiments, methods are provided that involve establishing COPD risk scores based on expression levels of informative-genes. In some embodiments, appropriate diagnostic intervention plans are established based at least in part on the COPD risk scores. In some embodiments, methods provided herein assist health care providers with making early and accurate diagnoses. In some embodiments, methods provided herein assist health care providers with establishing appropriate therapeutic interventions early on in patients' clinical evaluations. In some embodiments, methods provided herein involve evaluating biological samples obtained during bronchoscopies procedure. In some embodiments, the methods are beneficial because they enable health care providers to make informative decisions regarding patient diagnosis and/or treatment from otherwise uninformative bronchoscopies. In some embodiments, the risk assessment leads to appropriate surveillance for monitoring low risk lesions.

Provided herein are methods for determining the likelihood that a subject has COPD. The methods alone or in combination with other methods provide useful information for health care providers to assist them in making diagnostic and therapeutic decisions for a patient. The methods disclosed herein are often employed in instances where other methods have failed to provide useful information regarding the COPD status of a patient. For example, approximately 50% of bronchoscopy procedures result in indeterminate or non-diagnostic information. There are multiple sources of indeterminate results, and may depend on the training and procedures available at different medical centers. However, in certain embodiments, molecular methods in combination with bronchoscopy are expected to improve COPD assessment accuracy.

Methods disclosed herein provide alternative or complementary approaches for evaluating cell or tissue samples obtained by bronchoscopy procedures (or other procedures for evaluating respiratory tissue), and increase the likelihood that the procedures will result in useful information for managing the patient's care. The methods disclosed herein are highly sensitive, and produce information regarding the likelihood that a subject has COPD from cell or tissue samples (e.g., bronchial brushings of airway epithelial cells), which are often obtained from regions in the airway that are remote from malignant lung tissue. In general, the methods disclosed herein involve subjecting a biological sample obtained from a subject to a gene expression analysis to evaluate gene expression levels. However, in some embodiments, the likelihood that the subject has COPD is determined in further part based on the results of a histological examination of the biological sample or by considering other diagnostic indicia such as protein levels, mRNA levels, imaging results, chest X-ray exam results etc.

The term "subject," as used herein, generally refers to a mammal. Typically the subject is a human. However, the term embraces other species, e.g., pigs, mice, rats, dogs, cats, or other primates. In certain embodiments, the subject is an experimental subject such as a mouse or rat. The subject may be a male or female. The subject may be an infant, a toddler, a child, a young adult, an adult or a geriatric. The subject may be a smoker, a former smoker or a non-smoker. The subject may have a personal or family history of COPD or other lung disorder, including lung cancer. In some embodiments, the subject has one or more indicators that suggest COPD. In some embodiments, indicators that suggest COPD include dyspenea, which may be progressive (worsens over time), characteristically worse with exercise, and/or persistent; chronic cough, which may be intermittent and/or unproductive; chronic sputum production; history of tobacco smoke; history of exposure to smoke from home cooking and/or heating fuels; history of exposure to occupational dusts and chemicals; and/or a family history of COPD.

In some embodiments, the subject may exhibit one or more symptoms of COPD or other lung disorder. In some embodiments, the subject may have a new or persistent cough, worsening of an existing chronic cough, persistent bronchitis or repeated respiratory infections, chest pain, unexplained weight loss and/or fatigue, or breathing difficulties such as shortness of breath or wheezing. The subject may have a lesion, which may be observable by computer-aided tomography or chest X-ray. The subject may be a subject who has undergone a bronchoscopy or who has been identified as a candidate for bronchoscopy (e.g., because of the presence of a detectable lesion or suspicious imaging result). A subject under the care of a physician or other health care provider may be referred to as a "patient."

Informative-Genes

The expression levels of certain genes have been identified as providing useful information regarding the COPD status of a subject. These genes are referred to herein as "informative-genes." Informative-genes include protein coding genes and non-protein coding genes. It will be appreciated by the skilled artisan that the expression levels of informative-genes may be determined by evaluating the levels of appropriate gene products (e.g., mRNAs, miRNAs, proteins etc.) Accordingly, the expression levels of certain mRNAs have been identified as providing useful information regarding the lung cancer status of a subject. These mRNAs are referred to herein as "informative-mRNAs." Table 2 provide a listing of informative-genes that are differentially expressed in COPD.

Certain methods disclosed herein involve determining expression levels in the biological sample of at least one informative-gene. However, in some embodiments, the expression analysis involves determining the expression levels in the biological sample of at least 2, at least 3, at least 4, at least 5, at least 6, at least 7, at least 8, at least 9, at least 10, at least 20, at least 30, at least 40, at least 50, at least 60, at least 70, least 80, or at least 90 informative-genes.

In some embodiments, the number of informative-genes for an expression analysis are sufficient to provide a level of confidence in a prediction outcome that is clinically useful. This level of confidence (e.g., strength of a prediction model) may be assessed by a variety of performance parameters including, but not limited to, the accuracy, sensitivity specificity, and area under the curve (AUC) of the receiver operator characteristic (ROC). These parameters may be assessed with varying numbers of features (e.g., number of genes, mRNAs) to determine an optimum number and set of informative-genes. An accuracy, sensitivity or specificity of at least 60%, 70%, 80%, 90%, may be useful when used alone or in combination with other information.

Any appropriate system or method may be used for determining expression levels of informative-genes. Gene expression levels may be determined through the use of a hybridization-based assay. As used herein, the term, "hybridization-based assay" refers to any assay that involves nucleic acid hybridization. A hybridization-based assay may or may not involve amplification of nucleic acids. Hybridization-based assays are well known in the art and include, but are not limited to, array-based assays (e.g., oligonucleotide arrays, microarrays), oligonucleotide conjugated bead assays (e.g., Multiplex Bead-based Luminex® Assays), molecular inversion probe assays, and quantitative RT-PCR assays. Multiplex systems, such as oligonucleotide arrays or bead-based nucleic acid assay systems are particularly useful for evaluating levels of a plurality of genes simultaneously. Other appropriate methods for determining levels of nucleic acids will be apparent to the skilled artisan.

As used herein, a "level" refers to a value indicative of the amount or occurrence of a substance, e.g., an mRNA. A level may be an absolute value, e.g., a quantity of an mRNA in a sample, or a relative value, e.g., a quantity of an mRNA in a sample relative to the quantity of the mRNA in a reference sample (control sample). The level may also be a binary value indicating the presence or absence of a substance. For example, a substance may be identified as being present in a sample when a measurement of the quantity of the substance in the sample, e.g., a fluorescence measurement from a PCR reaction or microarray, exceeds a background value. Similarly, a substance may be identified as being absent from a sample (or undetectable in the sample) when a measurement of the quantity of the molecule in the sample is at or below background value. It should be appreciated that the level of a substance may be determined directly or indirectly.

Biological Samples

The methods generally involve obtaining a biological sample from a subject. As used herein, the phrase "obtaining a biological sample" refers to any process for directly or indirectly acquiring a biological sample from a subject. For example, a biological sample may be obtained (e.g., at a point-of-care facility, a physician's office, a hospital) by procuring a tissue or fluid sample from a subject. Alternatively, a biological sample may be obtained by receiving the sample (e.g., at a laboratory facility) from one or more persons who procured the sample directly from the subject.

The term "biological sample" refers to a sample derived from a subject, e.g., a patient. A biological sample typically comprises a tissue, cells and/or biomolecules. In some embodiments, a biological sample is obtained on the basis that it is histologically normal, e.g., as determined by endoscopy, e.g., bronchoscopy. In some embodiments, the biological sample is a sample of respiratory epithelium. The respiratory epithelium may be of the mouth, nose, pharynx, trachea, bronchi, bronchioles, or alveoli of the subject. The biological sample may comprise epithelium of the bronchi. In some embodiments, the biological sample is free of detectable cancer cells, e.g., as determined by standard histological or cytological methods. In some embodiments, histologically normal samples are obtained for evaluation. Often biological samples are obtained by scrapings or brushings, e.g., bronchial brushings. However, it should be appreciated that other procedures may be used, including, for example, brushings, scrapings, broncho-alveolar lavage, a bronchial biopsy or a transbronchial needle aspiration.

It is to be understood that a biological sample may be processed in any appropriate manner to facilitate determining expression levels. For example, biochemical, mechanical and/or thermal processing methods may be appropriately used to isolate a biomolecule of interest, e.g., RNA, from a biological sample. Accordingly, a RNA or other molecules may be isolated from a biological sample by processing the sample using methods well known in the art.

COPD Assessment

Methods disclosed herein may involve comparing expression levels of informative-genes with one or more appropriate references. An "appropriate reference" is an expression level (or range of expression levels) of a particular informative-gene that is indicative of a known COPD status. An appropriate reference can be determined experimentally by a practitioner of the methods or can be a pre-existing value or range of values. An appropriate reference represents an expression level (or range of expression levels) indicative of COPD. For example, an appropriate reference may be representative of the expression level of an informative-gene in a reference (control) biological sample obtained from a subject who is known to have COPD. When an appropriate reference is indicative of COPD, a lack of a detectable difference (e.g., lack of a statistically significant difference) between an expression level determined from a subject in need of characterization or diagnosis of COPD and the appropriate reference may be indicative of COPD in the subject. When an appropriate reference is indicative of COPD, a difference between an expression level determined from a subject in need of characterization or diagnosis of COPD and the appropriate reference may be indicative of the subject being free of COPD. In some embodiments, expression levels of informative-genes can be used to determine the severity of COPD in a subject.

Alternatively, an appropriate reference may be an expression level (or range of expression levels) of a gene that is indicative of a subject being free of COPD. For example, an appropriate reference may be representative of the expression level of a particular informative-gene in a reference (control) biological sample obtained from a subject who is known to be free of COPD. When an appropriate reference is indicative of a subject being free of COPD, a difference between an expression level determined from a subject in need of diagnosis of COPD and the appropriate reference may be indicative of COPD in the subject. Alternatively, when an appropriate reference is indicative of the subject being free of COPD, a lack of a detectable difference (e.g., lack of a statistically significant difference) between an expression level determined from a subject in need of diagnosis of COPD and the appropriate reference level may be indicative of the subject being free of COPD.

In some embodiments, the reference standard provides a threshold level of change, such that if the expression level of a gene in a sample is within a threshold level of change (increase or decrease depending on the particular marker) then the subject is identified as free of COPD, but if the levels are above the threshold then the subject is identified as being at risk of having COPD.

For example, increased expression of an mRNA that has a positive weight in the last column of Table 2, compared with the reference standard, is indicative of the subject having COPD. Furthermore, decreased expression of an mRNA that has a negative weight in the last column of Table 2, compared with the reference standard, is indicative of the subject having COPD.

The magnitude of difference between a expression level and an appropriate reference that is statistically significant may vary. For example, a significant difference that indicates COPD may be detected when the expression level of an informative-gene in a biological sample is at least 1%, at least 5%, at least 10%, at least 25%, at least 50%, at least 100%, at least 250%, at least 500%, or at least 1000% higher, or lower, than an appropriate reference of that gene. Similarly, a significant difference may be detected when the expression level of informative-gene in a biological sample is at least 1.1-fold, 1.2-fold, 1.5-fold, 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100-fold, or more higher, or lower, than the appropriate reference of that gene. In some embodiments, at least a 20% to 50% difference in expression between an informative-gene and appropriate reference is significant. Significant differences may be identified by using an appropriate statistical test. Tests for statistical significance are well known in the art and are exemplified in Applied Statistics for Engineers and Scientists by Petruccelli, Chen and Nandram 1999 Reprint Ed.

It is to be understood that a plurality of expression levels may be compared with plurality of appropriate reference levels, e.g., on a gene-by-gene basis. In order to assess the COPD status of the subject. The comparison may be made as a vector difference. In such cases, Multivariate Tests, e.g., Hotelling's $T^2$ test, may be used to evaluate the significance of observed differences. Such multivariate tests are well known in the art and are exemplified in Applied Multivariate Statistical Analysis by Richard Arnold Johnson and Dean W. Wichern Prentice Hall; $4^{th}$ edition (Jul. 13, 1998).

Classification Methods

The methods may also involve comparing a set of expression levels (referred to as an expression pattern or profile) of informative-genes in a biological sample obtained from a subject with a plurality of sets of reference levels (referred to as reference patterns), each reference pattern being associated with a known COPD status, identifying the reference pattern that most closely resembles the expression pattern, and associating the known COPD status of the reference pattern with the expression pattern, thereby classifying (characterizing) the COPD status of the subject.

The methods may also involve building or constructing a prediction model, which may also be referred to as a classifier or predictor, that can be used to classify the disease status of a subject. As used herein, a "COPD-classifier" is a prediction model that characterizes the COPD status of a subject based on expression levels determined in a biological sample obtained from the subject. Typically the model is built using samples for which the classification (COPD) has already been ascertained. Once the model (classifier) is built, it may then be applied to expression levels obtained from a biological sample of a subject whose COPD is unknown in order to predict the COPD status of the subject. Thus, the methods may involve applying a COPD-classifier to the expression levels, such that the COPD-classifier characterizes the COPD status of a subject based on the expression levels. The subject may be further treated or evaluated, e.g., by a health care provider, based on the predicted COPD status.

The classification methods may involve transforming the expression levels into a COPD risk-score that is indicative of the likelihood that the subject has COPD. In some embodiments, such as, for example, when a linear discriminant classifier is used, the COPD risk-score may be obtained as the combination (e.g., sum, product) of weighted expression levels, in which the expression levels are weighted by their relative contribution to predicting increased likelihood of having COPD.

It should be appreciated that a variety of prediction models known in the art may be used as a COPD-classifier. For example, a COPD-classifier may comprises an algorithm selected from logistic regression, partial least squares, linear discriminant analysis, quadratic discriminant analysis, neural network, naïve Bayes, C4.5 decision tree, k-nearest neighbor, random forest, and support vector machine or other appropriate method.

The COPD-classifier may be trained on a data set comprising expression levels of the plurality of informative-genes in biological samples obtained from a plurality of subjects identified as having COPD. For example, the COPD-classifier may be trained on a data set comprising expression levels of a plurality of informative-genes in biological samples obtained from a plurality of subjects identified as having COPD based histological findings. The training set will typically also comprise control subjects identified as not having COPD. As will be appreciated by the skilled artisan, the population of subjects of the training data set may have a variety of characteristics by design, e.g., the characteristics of the population may depend on the characteristics of the subjects for whom diagnostic methods that use the classifier may be useful. For example, the population may consist of all males, all females or may consist of both males and females. The population may consist of subjects with history of cancer, subjects without a history of cancer, or a subjects from both categories. The population may include subjects who are smokers, former smokers, and/or non-smokers. The population may include subjects who have lung cancer and/or subjects who not have lung cancer.

A class prediction strength can also be measured to determine the degree of confidence with which the model classifies a biological sample. This degree of confidence may serve as an estimate of the likelihood that the subject is of a particular class predicted by the model. Accordingly, the prediction strength conveys the degree of confidence of the classification of the sample and evaluates when a sample cannot be classified. There may be instances in which a sample is tested, but does not belong, or cannot be reliably assigned to, a particular class. This may be accomplished, for example, by utilizing a threshold, or range, wherein a sample which scores above or below the determined threshold, or within the particular range, is not a sample that can be classified (e.g., a "no call").

Once a model is built, the validity of the model can be tested using methods known in the art. One way to test the validity of the model is by cross-validation of the dataset. To perform cross-validation, one, or a subset, of the samples is eliminated and the model is built, as described above, without the eliminated sample, forming a "cross-validation model." The eliminated sample is then classified according to the model, as described herein. This process is done with all the samples, or subsets, of the initial dataset and an error rate is determined. The accuracy the model is then assessed. This model classifies samples to be tested with high accuracy for classes that are known, or classes have been previously ascertained. Another way to validate the model is to apply the model to an independent data set, such as a new biological sample having an unknown COPD status.

As will be appreciated by the skilled artisan, the strength of the model may be assessed by a variety of parameters including, but not limited to, the accuracy, sensitivity and specificity. Methods for computing accuracy, sensitivity and specificity are known in the art and described herein (See, e.g., the Examples). The COPD-classifier may have an accuracy of at least 60%, at least 65%, at least 70%, at least 75%, at least 80%, at least 85%, at least 90%, at least 95%, at least 99%, or more. The COPD-classifier may have an accuracy in a range of about 60% to 70%, 70% to 80%, 80% to 90%, or 90% to 100%. The COPD-classifier may have a sensitivity of at least 60%, at least 65%, at least 70%, at least 75%, at least 80%, at least 85%, at least 90%, at least 95%, at least 99%, or more. The COPD-classifier may have a sensitivity in a range of about 60% to 70%, 70% to 80%, 80% to 90%, or 90% to 100%. The COPD-classifier may have a specificity of at least 60%, at least 65%, at least 70%, at least 75%, at least 80%, at least 85%, at least 90%, at least 95%, at least 99%, or more. The COPD-classifier may have a specificity in a range of about 60% to 70%, 70% to 80%, 80% to 90%, or 90% to 100%.

Clinical Treatment/Management

In certain aspects, methods are provided for determining a treatment course for a subject. The methods typically involve determining the expression levels in a biological sample obtained from the subject of one or more informative-genes, and determining a treatment course for the subject based on the expression levels. Often the treatment course is determined based on a COPD risk-score derived from the expression levels. The subject may be identified as a candidate for a COPD therapy based on a COPD risk-score that indicates the subject has a relatively high likelihood of having COPD. The subject may be identified as a candidate for an invasive lung procedure (e.g., transthoracic needle aspiration, mediastinoscopy, or thoracotomy) based on a COPD risk-score that indicates the subject has a relatively high likelihood of having COPD (e.g., greater than 60%, greater than 70%, greater than 80%, greater than 90%). The subject may be identified as not being a candidate for a COPD therapy or an invasive lung procedure based on a COPD risk-score that indicates the subject has a relatively low likelihood (e.g., less than 50%, less than 40%, less than 30%, less than 20%) of having COPD. In some cases, an intermediate risk-score is obtained and the subject is not indicated as being in the high risk or the low risk categories. In some embodiments, a health care provider may engage in "watchful waiting" and repeat the analysis on biological samples taken at one or more later points in time, or undertake further diagnostics procedures to rule out COPD, or make a determination that COPD is present, soon after the risk determination was made. The methods may also involve creating a report that summarizes the results of the gene expression analysis. Typically the report would also include an indication of the COPD risk-score.

Computer Implemented Methods

Methods disclosed herein may be implemented in any of numerous ways. For example, certain embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, aspects of the invention may be embodied as a computer readable medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other non-transitory, tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above. As used herein, the term "non-transitory computer-readable storage medium" encompasses only a computer-readable medium that can be considered to be a manufacture (i.e., article of manufacture) or a machine.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

As used herein, the term "database" generally refers to a collection of data arranged for ease and speed of search and retrieval. Further, a database typically comprises logical and physical data structures. Those skilled in the art will recognize the methods described herein may be used with any type of database including a relational database, an object-relational database and an XML-based database, where XML stands for "eXtensible-Markup-Language". For example, the gene expression information may be stored in and retrieved from a database. The gene expression information may be stored in or indexed in a manner that relates the gene expression information with a variety of other relevant information (e.g., information relevant for creating a report or document that aids a physician in establishing treatment protocols and/or making diagnostic determinations, or information that aids in tracking patient samples). Such relevant information may include, for example, patient identification information, ordering physician identification information, information regarding an ordering physician's office (e.g., address, telephone number), information regarding the origin of a biological sample (e.g., tissue type, date of sampling), biological sample processing information, sample quality control information, biological sample storage information, gene annotation information, COPD risk classifier information, COPD risk factor information, payment information, order date information, etc.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

In some aspects of the invention, computer implemented methods for processing genomic information are provided. The methods generally involve obtaining data representing expression levels in a biological sample of one or more informative-genes and determining the likelihood that the subject has COPD based at least in part on the expression levels. Any of the statistical or classification methods disclosed herein may be incorporated into the computer implemented methods. In some embodiments, the methods involve calculating a risk-score indicative of the likelihood that the subject has COPD. Computing the risk-score may involve a determination of the combination (e.g., sum, product or other combination) of weighted expression levels, in which the expression levels are weighted by their relative contribution to predicting increased likelihood of having COPD. The computer implemented methods may also involve generating a report that summarizes the results of the gene expression analysis, such as by specifying the risk-score. Such methods may also involve transmitting the report to a health care provider of the subject.

Compositions and Kits

In some aspects, compositions and related methods are provided that are useful for determining expression levels of informative-genes. For example, compositions are provided that consist essentially of nucleic acid probes that specifically hybridize with informative-genes or with nucleic acids having sequences complementary to informative-genes. These compositions may also include probes that specifically hybridize with control genes or nucleic acids complementary thereto. These compositions may also include appropriate buffers, salts or detection reagents. The nucleic acid probes may be fixed directly or indirectly to a solid support (e.g., a glass, plastic or silicon chip) or a bead (e.g., a magnetic bead). The nucleic acid probes may be customized for used in a bead-based nucleic acid detection assay.

In some embodiments, compositions are provided that comprise up to 5, up to 10, up to 25, up to 50, up to 100, or up to 200 nucleic acid probes. In some cases, each of the nucleic acid probes specifically hybridizes with an mRNA selected from Table 2 or with a nucleic acid having a sequence complementary to the mRNA. In some embodiments, probes that detect informative-mRNAs are also included. In some cases, each of at least 2, at least 3, at least 4, at least 5, at least 6, at least 7, at least 8, at least 9, at least 10, or at least 20 of the nucleic acid probes specifically hybridizes with an mRNA selected from Table 2 or with a nucleic acid having a sequence complementary to the mRNA. The compositions may be prepared for detecting different genes in biochemically separate reactions, or for detecting multiple genes in the same biochemical reactions.

Also provided herein are oligonucleotide (nucleic acid) arrays that are useful in the methods for determining levels of multiple informative-genes simultaneously. Such arrays may be obtained or produced from commercial sources. Methods for producing nucleic acid arrays are also well known in the art. For example, nucleic acid arrays may be constructed by immobilizing to a solid support large numbers of oligonucleotides, polynucleotides, or cDNAs capable of hybridizing to nucleic acids corresponding to genes, or portions thereof. The skilled artisan is referred to Chapter 22 "Nucleic Acid Arrays" of Current Protocols In Molecular Biology (Eds. Ausubel et al. John Wiley and #38; Sons NY, 2000) or Liu C G, et al., *An oligonucleotide microchip for genome-wide microRNA profiling in human and mouse tissues. Proc Natl Acad Sci USA.* 2004 Jun. 29; 101(26):9740-4, which provide non-limiting examples of methods relating to nucleic acid array construction and use in detection of nucleic acids of interest. In some embodiments, the arrays comprise, or consist essentially of, binding probes for at least 2, at least 5, at least 10, at least 20, at least 50, at least 60, at least 70 or more informative-genes. In some embodiments, the arrays comprise, or consist essentially of, binding probes for up to 2, up to 5, up to 10, up to 20, up to 50, up to 60, up to 70 or more informative-genes. In some embodiments, an array comprises or consists of 1, 2, 3, 4, 5, 6, 7, 8, 9, or 10 of the mRNAs selected from Table 2. In some embodiments, an array comprises or consists of 4, 5, or 6 of the mRNAs selected from Table 2. Kits comprising the oligonucleotide arrays are also provided. Kits may include nucleic acid labeling reagents and instructions for determining expression levels using the arrays.

The compositions described herein can be provided as a kit for determining and evaluating expression levels of informative-genes. The compositions may be assembled into diagnostic or research kits to facilitate their use in diagnostic or research applications. A kit may include one or more containers housing the components of the invention and instructions for use. Specifically, such kits may include one or more compositions described herein, along with instructions describing the intended application and the proper use of these compositions. Kits may contain the components in appropriate concentrations or quantities for running various experiments.

The kit may be designed to facilitate use of the methods described herein by researchers, health care providers, diagnostic laboratories, or other entities and can take many forms. Each of the compositions of the kit, where applicable, may be provided in liquid form (e.g., in solution), or in solid form, (e.g., a dry powder). In certain cases, some of the compositions may be constitutable or otherwise processable, for example, by the addition of a suitable solvent or other substance, which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of diagnostic or biological products, which instructions can also reflect approval by the agency.

A kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The components may be in the form of a liquid, gel or solid (e.g., powder). The components may be prepared sterilely and shipped refrigerated. Alternatively they may be housed in a vial or other container for storage. A second container may have other components prepared sterilely.

As used herein, the terms "approximately" or "about" in reference to a number are generally taken to include numbers that fall within a range of 1%, 5%, 10%, 15%, or 20% in either direction (greater than or less than) of the number unless otherwise stated or otherwise evident from the context (except where such number would be less than 0% or exceed 100% of a possible value).

All references described herein are incorporated by reference for the purposes described herein.

Exemplary embodiments of the invention will be described in more detail by the following examples. These embodiments are exemplary of the invention, which one skilled in the art will recognize is not limited to the exemplary embodiments.

EXAMPLES

Example 1: Gene Expression Analysis of Bronchoscopy Samples

Applicants collected several hundred clinical samples comprising bronchial epithelial cells obtained during routine bronchoscopy. Subjects were enrolled in the trial due to a suspicion of lung cancer who had been referred to a pulmonologist for bronchoscopy. A majority of the subjects were subsequently confirmed to have lung cancer by histological and pathological examination of cells taken from the lung either during bronchoscopy, or during some follow-up procedure. A minority of subjects were found to be cancer free at the time of presentation to the pulmonologist and up to 12 months following that date. Samples were utilized to develop a gene expression test to predict subjects with the highest risk of cancer in cases where bronchoscopy yields a non-positive result. The combination of false-negative cases (which occurs in 25-30% of the cancer cases) and the true-negative cases yield a combined set of non-positive bronchoscopy procedures, representing approximately 40-50% of the total cases referred to pulmonologists.

Applicants established a set of genes that are differentially expressed between subjects with and without cancer. Furthermore the expression intensities of these genes (representing both up- and down-regulated genes) were combined using multivariate classifier algorithms to yield a "score" which was used to predict subjects with and without cancer. The resulting test was shown to have high sensitivity and specificity and therefore add diagnostic value in cases where bronchoscopy is non-positive.

Applicants have developed methods to improve test specificity. Applicants have identified factors in the sample cohorts used to "train" and "test" the algorithm that influence test specificity. Two factors, which are related, were identified as subjects previously diagnosed with COPD and subjects indicated to be using inhaled medications (e.g., bronchodilators and corticosteroids). COPD is estimated to yield a 5-fold increase in lung cancer risk, compared to smokers without COPD.

Applicants have established sets of genes that distinguish smokers (current or former) with and without lung cancer based on airway field of injury. Specifically, RNA isolated from cytologically normal appearing cells collected from the bronchus of suspect lung cancer patients was used to generate a gene expression signature that predicts the risk of lung cancer with high accuracy. Applicants have determined that specificity of this gene signature differs between subjects with and without COPD (Table 1). Specifically, subjects with COPD but not cancer have significantly lower specificity than subjects with neither indication. There is less of a difference in prediction sensitivity of the signature between COPD positive and negative cases.

TABLE 1

Cancer risk prediction specificity and sensitivity of subjects with and without COPD

| | PY cutoff | | | | | | |
|---|---|---|---|---|---|---|---|
| | NC, w/COPD | | NC, w/o COPD | | CA, w/COPD | | CA, w/o COPD |
| | Specificity | | Specificity | | Specificity | | Specificity |
| TOTAL | 42 | 30.5% | 99 | 70.6% | 168 | 80.2% | 257 | 68.1% |

Example 2: Identification of Differentially Expressed Genes Associated with Chronic Obstructive Pulmonary Disease Applicant sought to determine whether genes are differentially expressed between subjects with and without COPD (all of which are cancer-free). Applicants sought to determine if the expression levels of those genes could be combined in order to predict COPD cases, in subjects without lung cancer. COPD is a major risk of lung cancer and identification of subjects with COPD may be an effective means of identifying subjects who will likely develop cancer which ultimately could be used as an effective early detection method. Furthermore, by identifying genes associated with COPD, some of these may be shown to be effective drug-targets for chemoprevention strategies.

Applicants found that a total of 1833 genes are differentially expressed (p≤0.05) after applying a false-discovery rate correction. Applicants further found that gene expression intensities could be combined using well-known classifier algorithms [e.g., Linear Discriminant Analysis (LDA), or Support Vector Machine (SVM)] to generate "scores". The scores can then be used to distinguish COPD-positive and COPD-negative cases relative to a threshold. Applicants found that gene signatures comprising different numbers of individual genes led to effective predictions of COPD. For a given combination of genes the sensitivity and specificity of the algorithm (or signature) was determined by comparison to previously diagnosed cases, with and without COPD. The sensitivity and specificity depends on the threshold value, and a Receiver Operator Characteristic (ROC) curve was constructed. An example is shown in FIG. 1. In this case the overall Area Under the Curve (AUC) of the ROC curve is 0.81 and can be used as an indicator of overall accuracy of a gene-signature, where AUC=1 is 100% accuracy and AUC=0.5 is equivalent to a random predictor.

A list of the top 100 differentially expressed genes is shown in Table 2, along with the weight calculated for each gene. The greater the absolute value of the weight, the more significant the importance of the gene to differentiate subjects with and without COPD.

TABLE 2

The top 100 differentially expressed genes for predicting COPD

| Gene | Regression Weights |
| --- | --- |
| PCDH7 | −6.58E−01 |
| CCDC81 | −6.54E−01 |
| CEACAM5 | 6.02E−01 |
| PTPRH | 6.01E−01 |
| C12orf36 | 5.81E−01 |
| B3GNT6 | 5.60E−01 |
| PLAG1 | −5.59E−01 |
| PDE7B | −5.54E−01 |
| CACHD1 | −5.48E−01 |
| EPB41L2 | −5.44E−01 |
| FRMD4A | −5.42E−01 |
| PRKCE | −5.40E−01 |
| SULF1 | −5.38E−01 |
| TLE1 | 5.30E−01 |
| FAM114A1 | 5.25E−01 |
| ELF5 | −5.24E−01 |
| SGCE | −5.21E−01 |
| SEC14L3 | −5.18E−01 |
| GPR155 | −5.15E−01 |
| ITGA9 | −5.14E−01 |
| PTGFR | −5.13E−01 |
| ISLR | −5.08E−01 |
| SLC5A7 | −5.07E−01 |
| ZNF483 | −5.03E−01 |
| DPYSL3 | 5.02E−01 |
| TNS3 | −5.01E−01 |
| FMNL2 | −4.97E−01 |
| GALE | 4.95E−01 |
| CNTN3 | −4.95E−01 |
| HSD17B13 | −4.94E−01 |
| PTPRM | −4.93E−01 |
| HLF | −4.93E−01 |
| PROS1 | −4.90E−01 |
| PLA2G4A | 4.90E−01 |
| KAL1 | −4.89E−01 |
| TCN1 | 4.88E−01 |
| DPP4 | −4.85E−01 |
| GPR98 | −4.84E−01 |
| KCNA1 | −4.83E−01 |
| CABLES1 | −4.82E−01 |
| PEG10 | −4.82E−01 |
| PPP1R9A | −4.81E−01 |
| POLA2 | −4.78E−01 |
| C17orf37 | 4.78E−01 |
| ABCC4 | −4.78E−01 |
| CA8 | −4.76E−01 |
| CYP2A13 | −4.76E−01 |
| SETBP1 | −4.75E−01 |
| ANKS1B | −4.75E−01 |
| CHP | 4.75E−01 |
| THSD4 | −4.72E−01 |
| MPDU1 | 4.72E−01 |
| CD109 | 4.71E−01 |
| STK32A | −4.70E−01 |
| HHLA2 | −4.70E−01 |
| AMMECR1 | 4.69E−01 |
| NPAS3 | −4.68E−01 |
| GXYLT2 | −4.67E−01 |
| KLF12 | −4.67E−01 |
| CA12 | 4.67E−01 |
| C21orf121 | −4.67E−01 |
| SH3BP4 | 4.66E−01 |
| FABP6 | −4.64E−01 |
| GUCY1B3 | 4.64E−01 |
| FUT3 | 4.62E−01 |
| STX10 | 4.61E−01 |
| FTO | −4.61E−01 |
| CNTN4 | −4.59E−01 |
| ATP8A1 | −4.59E−01 |
| GMDS | 4.57E−01 |
| ZNF671 | −4.57E−01 |
| WBP5 | 4.57E−01 |
| MYO5B | 4.57E−01 |
| FLRT3 | −4.56E−01 |
| SCGB1A1 | −4.55E−01 |
| SCNN1G | −4.55E−01 |
| CFTR | −4.55E−01 |
| LOC339524 | −4.53E−01 |
| THSD7A | −4.53E−01 |
| CACNB4 | −4.52E−01 |
| DQX1 | 4.52E−01 |
| GLI3 | −4.52E−01 |
| NFAT5 | −4.50E−01 |
| RUNX1T1 | −4.50E−01 |
| SNTB1 | −4.50E−01 |
| C16orf89 | −4.48E−01 |
| PRKD1 | −4.48E−01 |
| ANXA6 | −4.48E−01 |
| YIPF1 | 4.48E−01 |
| ATP10B | 4.46E−01 |
| HK2 | 4.46E−01 |
| ABHD2 | 4.45E−01 |
| DNAH5 | −4.45E−01 |
| GGT7 | −4.45E−01 |
| FBN1 | −4.44E−01 |
| PRSS12 | −4.44E−01 |
| TMPRSS4 | 4.42E−01 |
| AMIGO2 | −4.41E−01 |
| TMEM54 | 4.40E−01 |
| CAPRIN2 | −4.40E−01 |

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method for processing a biological sample of a subject, comprising:
    (a) obtaining said biological sample from a bronchial epithelium of said subject;
    (b) subjecting a first portion of said biological sample to histological or cytological testing that indicates that said first portion of said biological sample is free of detectable cancer cells;
    (c) upon identifying that said first portion of said biological sample is free of detectable cancer cells, using nucleic acid hybridization, amplification, or sequencing to generate a first data set with a level of gene expression products of a plurality of genes comprising PCDH7 and PTPRH from a second portion of said biological sample, which gene expression products are differentially expressed as compared to a reference;
    (d) processing said first data set to obtain a second data set comprising a COPD risk-score for said biological sample; and
    (e) outputting a report having said COPD risk score.

2. The method of claim 1, wherein (c) comprises using probes having sequence complementarity with gene expression products of said plurality of genes comprising PCDH7 and PTPRH.

3. The method of claim 1, wherein said subject exhibits one or more symptoms of COPD or has a lesion that is observable by computer aided tomography or chest x-ray.

4. The method of claim 3, wherein, prior to subjecting said first portion of said biological sample to histological or cytological testing, said subject has not been diagnosed with COPD.

5. The method of claim 1, wherein said COPD risk-score is (i) a combination of weighted gene expression product levels or (ii) a sum of weighted gene expression product levels.

6. The method of claim 5, wherein said weighted expression levels are weighted by their relative contribution to predicting increased likelihood of having COPD.

7. The method of claim 1, further comprising determining a treatment course based on said COPD risk-score.

8. The method of claim 6, wherein said subject is either: (i) a candidate for a COPD therapy and/or an invasive lung procedure based on said COPD risk score indicating that said subject has a relatively high likelihood of having COPD; or (ii) not a candidate for a COPD therapy or an invasive lung procedure based on said COPD risk-score indicating that said subject has a relatively low likelihood of having COPD.

9. The method of claim 1, wherein said biological sample is obtained using bronchial brushing, broncho-alveolar lavage, or a bronchial biopsy.

10. The method of claim 1, wherein said plurality of genes comprises at least 3 additional genes selected from the group consisting of: CCDC81, CEACAM5, C12orf36, B3GNT6, PLAG1, PDE7B, CACHD1, EPB41L2, FRMD4A, PRKCE, ZNF483, DPYSL3, TNS3, FMNL2, GALE, CNTN3, HSD17B13, PTPRM, HLF, PROS1, PLA2G4A, KAL1, TCN1, DPP4, GPR98, KCNA1, CABLES1, PEG10, PPP1R9A, POLA2, C17orf37, ABCC4, CA8, CYP2A13, SETBP1, ANKS1B, CHP, THSD4, MPDU1, CD109, STK32A, HHLA2, AMMECR1, NPAS3, GXYLT2, KLF12, CA12, C21orf121, SH3BP4, FABP6, GUCY1B3, FUT3, STX10, FTO, CNTN4, ATP8A1, GMDS, ZNF671, WBPS, MYO5B, FLRT3, SCGB1A1, SNTB1, C16orf89, PRKD1, ANXA6, YIPF1, ATP10B, HNK, ABHD2, DNAH5, GGT7, FBN1, PRSS12, TMPRSS4, AM1GO2, TMEM54, or CAPRIN2.

11. The method of claim 1, wherein said COPD risk-score is a combination of weighted gene expression product levels.

12. The method of claim 1, wherein said COPD risk-score is a sum of weighted gene expression product levels.

* * * * *